United States Patent
Robinson

(10) Patent No.: US 6,697,660 B1
(45) Date of Patent: Feb. 24, 2004

(54) METHOD FOR FUNCTIONAL BRAIN IMAGING FROM MAGNETOENCEPHALOGRAPHIC DATA BY ESTIMATION OF SOURCE SIGNAL-TO-NOISE RATIO

(75) Inventor: Stephen E. Robinson, Maple Ridge (CA)

(73) Assignee: CTF Systems, Inc., British Columbia (CA)

( * ) Notice: Subject to any disclaimer, the term of this patent is extended or adjusted under 35 U.S.C. 154(b) by 0 days.

(21) Appl. No.: 09/138,826

(22) Filed: Aug. 24, 1998

Related U.S. Application Data

(60) Provisional application No. 60/072,340, filed on Jan. 23, 1998.

(51) Int. Cl.[7] .................................................. A61B 5/05
(52) U.S. Cl. ........................ 600/409; 382/128; 324/248
(58) Field of Search .............................. 600/409, 544, 600/407; 128/920, 922; 382/128; 324/248, 260, 244

(56) References Cited

U.S. PATENT DOCUMENTS

| | | | |
|---|---|---|---|
| 4,408,616 A | 10/1983 | Duffy et al. | |
| 4,947,480 A | 8/1990 | Lewis | |
| 4,949,725 A | 8/1990 | Raviv et al. | |
| 4,977,896 A | 12/1990 | Robinson et al. | |
| 5,136,242 A | 8/1992 | Abraham-Fuchs | |
| 5,170,119 A | 12/1992 | Sekihara et al. | |
| 5,228,443 A | 7/1993 | Tatar | |
| 5,263,488 A | 11/1993 | Van Veen et al. | |
| 5,269,325 A | 12/1993 | Robinson et al. | |
| 5,285,385 A | * 2/1994 | Igarashi et al. | |
| 5,307,807 A | 5/1994 | Valdes Sosa et al. | |

(List continued on next page.)

FOREIGN PATENT DOCUMENTS

| | | | |
|---|---|---|---|
| DE | 43 26 041 | * | 4/1994 |
| DE | 43 26 043 | * | 4/1994 |
| DE | 43 26 044 | * | 4/1994 |
| JP | 5-015504 | * | 1/1993 |
| JP | 6-245916 | * | 9/1994 |

*Primary Examiner*—Marvin M. Lateef
*Assistant Examiner*—Shawna J. Shaw
(74) *Attorney, Agent, or Firm*—Townsend and Townsend and Crew LLP; Kenneth R. Allen

(57) ABSTRACT

An improved method, termed "statistical synthetic aperture magnetometry" (SSAM) of transforming magnetoencephalographic (MEG) measurements into corresponding three-dimensional images of the electrophysiological activity within the brain. The computed images are static, representing the time-integrated brain activity over a selected period. By selecting the time periods and frequency bands of interest, the SSAM method selectively images brain activity relating to different types of brain pathology or to cognitive events. Unlike prior art methods, the SSAM method compensates for the growth of ionic signal source strength estimates with depth into the head, resulting, in part, from the declining sensitivity of the MEG sensors. This is achieved by computing and displaying functions of the ratio of source strength to its noise for each element comprising the image. That is, a functional image is determined by an array of voxels where each voxel is based upon a function of source signal-to-noise ratio (SNR) rather than the source strength, alone. By using functions of SNR to represent source activity, the SSAM method achieves more accurate and higher resolution source localization. Each voxel is represented as a function of the ratio of a source power estimate to a source noise variance estimate. Such functions are found to be maximum at the true locations of sources, whereas plots of source power alone (as in prior art methods), show maxima which appear deeper and more diffuse in the brain than they in fact are.

29 Claims, 8 Drawing Sheets

U.S. PATENT DOCUMENTS

| | | |
|---|---|---|
| 5,315,308 A | 5/1994 | Nehorai et al. |
| 5,392,210 A | 2/1995 | Scholz |
| 5,417,211 A * | 5/1995 | Abraham-Fuchs et al. |
| 5,426,365 A | 6/1995 | Sekihara et al. |
| 5,511,008 A | 4/1996 | Flament et al. |
| 5,524,086 A | 6/1996 | Kiyuna |
| 5,526,811 A | 6/1996 | Lypchuk |
| 5,594,849 A | 1/1997 | Kuc et al. |
| 5,601,081 A | 2/1997 | Tomita et al. |
| 5,671,740 A | 9/1997 | Tomita et al. |
| 5,682,889 A | 11/1997 | Tomita et al. |
| 5,687,724 A | 11/1997 | Jewett et al. |
| 5,701,909 A | 12/1997 | Amir et al. |
| 5,730,131 A | 3/1998 | Ohyu |
| 5,752,514 A * | 5/1998 | Okamura et al. |
| 5,755,227 A | 5/1998 | Tomita et al. |
| 5,885,215 A * | 3/1999 | Dossel et al. |

\* cited by examiner

COMPUTING A TOMOGRAPHIC IMAGE OF SITES OF ABNORMAL BRAIN ACTIVITY FROM MEG EPILEPSY DATA, BY APPLICATION OF STATISTICAL SYNTHETIC APERTURE MAGNETOMETRY

METHOD FOR FUNCTIONAL BRAIN IMAGING FROM MAGNETOENCEPHALOGRAPHIC DATA BY ESTIMATION OF SOURCE SIGNAL-TO-NOISE RATIO

REFERENCE TO RELATED APPLICATION

This application is a continuation-in-part of, and claims the benefit of, U.S. Provisional Application No. 60/072,340 filed Jan. 23, 1998.

TECHNICAL FIELD

This invention is directed to a method of transforming magnetoencephalographic (MEG) measurements into corresponding three-dimensional images of the electrophysiological activity within the brain. Image blurring due to ambiguity of source depth is greatly reduced by computing and displaying a measure of the proportion of source strength to noise for each discrete element comprising the image, to achieve more accurate and higher resolution source localization.

BACKGROUND

Methods and instrumentation for generating functional images of human brain activity are of great importance for diagnosis of clinical brain disorders. Moreover, it is important that a functional imaging technology be non-invasive, providing a favourable risk-benefit ratio for patients and extending its application to fundamental neuropsychological research. "Functional brain imaging" implies a method that measures and displays brain activity, or some parameter relating to brain activity, as a function of a three-dimensional position within the head. When combined or fused with an anatomical image of the head, such as from a magnetic resonance image (MRI) or computed tomography (CT) scan, a functional brain image relates the level of brain activity to specific anatomical structures within the brain. Observing changes in the level of brain activity at specific loci helps persons skilled in the art understand how the brain operates in both health and disease conditions.

U.S. Provisional Application No. 60/072,340 filed Jan. 23, 1998 which is incorporated herein by reference, discloses an analytic method called "synthetic aperture magnetometry" (SAM), that is useful for transforming magnetoencephalographic (MEG) signals into corresponding functional brain images. However, if the SAM method is used to compute functional brain images, without using background or control state subtraction, the signal source strength estimates tend to get progressively stronger toward the center of the head. This results in an ambiguity of source depth, while resolving source features on a surface of constant depth. The progressive image "blur" with depth is not in agreement with acceptable neurophysiological data. However, when the SAM method is used to estimate differential images, comparing control and active brain states, the ambiguity in source depth is greatly reduced, but not eliminated. The differential mode is therefore the preferred mode of using the SAM method.

The present invention provides an improved method, termed "statistical synthetic aperture magnetometry" (SSAM). Like the SAM method, the SSAM method transforms MEG measurements into corresponding three-dimensional images of the electrophysiological activity within the brain. The computed images are static, representing the time-integrated brain activity over some selected period. Furthermore, by selecting frequency bands of interest, the SSAM method selectively images brain activity relating to different types of brain pathology or to cognitive events. The SSAM method uses the SAM method to compute both a source estimate and a noise estimate. However, unlike the SAM method, the SSAM method compensates for the growth of the source strength estimate with depth into the head. Such compensation is achieved by computing and displaying an image for which each element represents a function of the ratio of source strength to noise. That is, each image element (termed a "voxel" for volume images and "pixel" for planar image) is based upon the source signal-to-noise ratio (SNR) rather than the source strength, alone. By using SNR or a derivative function to represent source activity the SSAM method achieves more accurate and higher resolution source localization. The SAM method computes the root mean square (RMS) source estimate, on a voxel-by-voxel basis. However, it is also possible to use the SAM method to compute an estimate of the voxel uncorrelated noise. The SSAM method represents each image element as some function of the ratio of a source power estimate to a source noise variance estimate. Such functions are found to be maximum at the true locations of sources, whereas plots of source power alone (as in the SAM method), show maxima which appear deeper in the brain than in fact are.

The SSAM method lends itself to imaging both differential and non-differential brain activities. In differential mode, one compares the SNR of one state of brain activity (e.g., "active") to another state (e.g., "control"); forming the appropriate combinations may compare two or more states of brain activity. These comparisons may be made either on a voxel-by-voxel basis, or by forming multiple-voxel statistical quantities. The comparison images may be expressed as a T (difference) or F (ratio) statistics. SSAM may also be used to transform MEG measurements into non-comparison functional brain images. The non-differential images are usually cast as z-statistics. The new functional images are computed from the statistics associated with each image element. The statistics used may be signal-to-noise ratio (SNR), functions of SNR, ratios of SNRs, differences, etc. When cast in the framework of existing z, T, or F-statistics, one can compute probability values representing the statistical significance of the activity. Thus, a functional image can be generated from the p-values.

The average MEG sensor measurement noise is estimated from the least-significant singular value of a measurement covariance matrix, following singular value decomposition (SVD), as this represents the spatial mode having the smallest signal power.

Unlike the SAM method, which maps root mean square (RMS) source power, the quantity that is mapped by the SSAM method is either the z-statistic, T-statistic, or a derived probability statistic of that power. The SSAM method results in a highly significant improvement in image quality over that attainable by the SAM method or by other currently available MEG image transforms. Specifically, the SSAM method improves image contrast and resolution, such that activity within deep structures of the brain can be observed separately from superficial sources. Thus, the SSAM method does not represent a trivial change in the units that are mapped from dipole power to a statistical representation of the dipole power. The SSAM method has been reduced to practice and has been demonstrated to image abnormal high and low frequency brain activity in cases of epilepsy, and can also map the brain areas relating to the production of speech.

SUMMARY OF THE INVENTION

In accordance with the preferred embodiment, the invention provides a method of making a functional image of a subject's brain from magnetoencephalographic measurements. A plurality of magnetoencephalographic data signals are simultaneously collected from a plurality of sensors surrounding the brain. An array of voxel coordinates is selected, relative to the sensors, such that the voxels define a region of interest within the brain. The covariance of the measured data signals is then determined, together with the sensors' uncorrelated noise variance. These quantities facilitate determination, for each voxel, a "source power", being the mean-square source current dipole moment. The uncorrelated noise variance for each voxel is then determined, followed by a determination, for each voxel, of a function of the voxels' source power and uncorrelated noise variance. The function is then further processed into derivative statistics, or is converted directly into a false-color or gray-scale functional image of source activity. This functional image is then coregistered with a predefined anatomical image. The coregistered images can then be displayed.

Either before or after time-sampling, the collected MEG data signals are frequency domain filtered to exclude signal frequencies outside a selected frequency range. For example, the selected frequency range may be characteristic of a selected brain activity.

The source power to noise variance ratio for each image element $$\rho_\theta = \frac{S_\theta^2}{\sigma_\theta^2}$$

is determined. If desired, a corrected estimate of source power can be derived by subtracting the noise variance from the mean-square source moment, for each image element. Advantageously, a z-statistic representation of the source power to noise variance ratio is determined, for example $z_\theta = [\rho_\theta]^{1/2}$.

The previously described method can also be used to determine an active source power to noise variance ratio $^{(a)}\rho_\theta$ while the subject's brain is engaged in a particular activity; and, to determine a control source power to noise variance ratio $^{(c)}\rho_\theta$ while the subject's brain is at rest. A ratio of the active and control source power to noise variance ratios $$^{(a:c)}\eta_\theta = \frac{^{(a)}\rho_\theta}{^{(c)}\rho_\theta}$$

is then derived for each image element. The ratio of the active and control source power to noise variance ratios is then converted into a false-color or gray-scale functional image of source activity, which is in turn coregistered with a predefined anatomical image. The coregistered images are then displayed.

A functional image derived from comparison of active and control conditions may also be made in the form of T-statistics for each image element. For example:

$$^{(a-c)}T_\theta = \left[\frac{n|^{(a)}S_\theta^2 - ^{(c)}S_\theta^2|}{^{(a)}\sigma_\theta^2 + ^{(c)}\sigma_\theta^2}\right]^{1/2}$$

Even though this expression is not the source power to noise variance ratio, the desirable properties of the invention are retained—namely improved spatial resolution and contrast of source activity in three dimensions. This can be seen as a consequence of the T-statistic being a measure of the ratio of source strength to noise.

Figure 1:
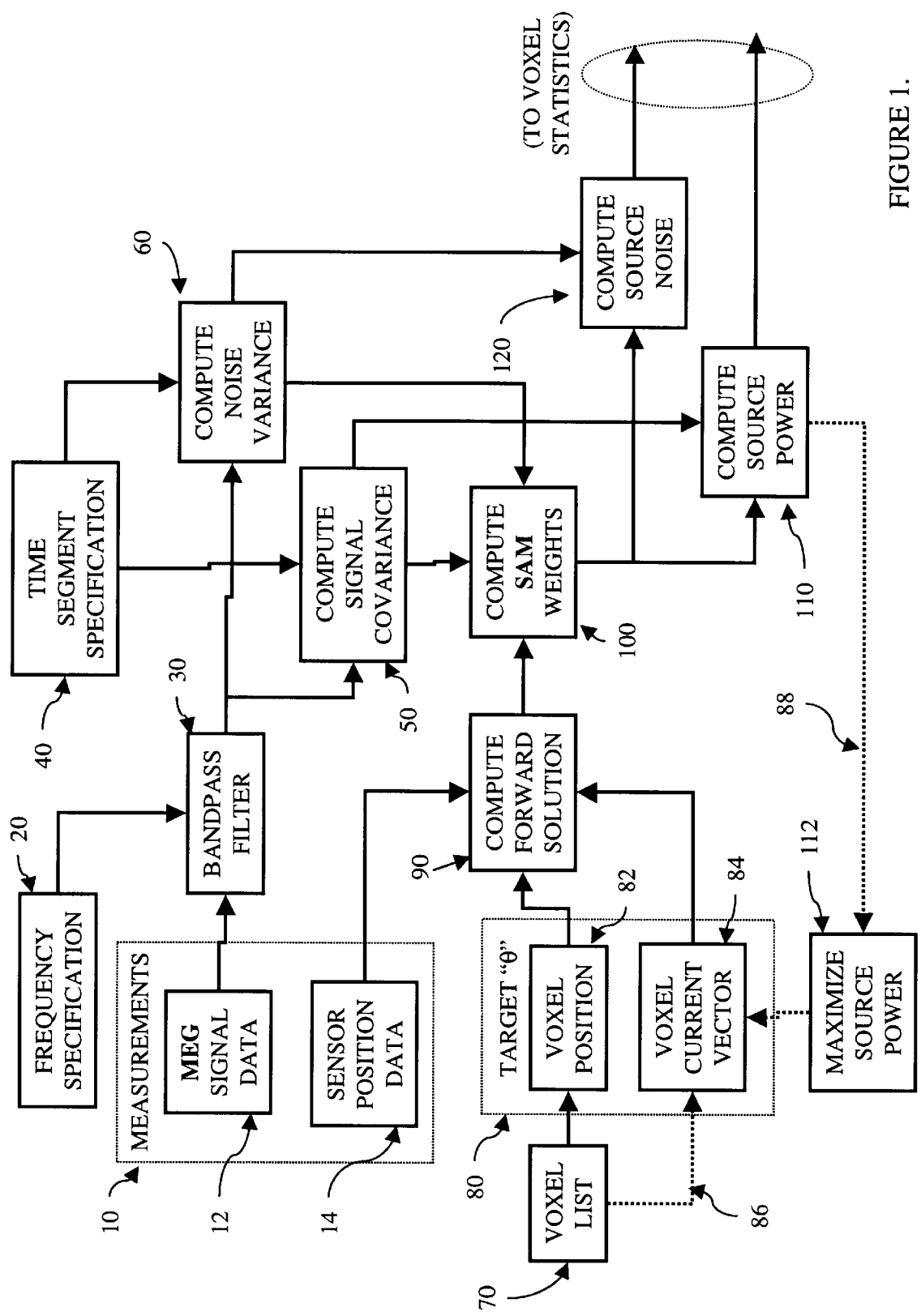
FIG. 1 is a flowchart which depicts the preferred sequence of steps for determining source noise and source power in accordance with the invention.

DESCRIPTION (i) Background (1) Comparison of Source Estimation with Inverse Solution There are two general classes of analyses for transforming MEG and/or EEG measurements into corresponding maps of location and intensity of brain activity. These two classes are referred to as "inverse solution" and "source estimation". The following sections clarify the differences between these two classes.

All inverse solution methods are based upon minimizing the difference between the measured values and those predicted from a model. The minimization is usually computed using least-squares methods. The predicted measurements are based upon a mathematical model describing the brain's ionic current sources, the conducting space of the head (including all boundaries and anisotropy), and the theoretical response of the measurement sensors employed. The parameters describing the ionic current sources (position, orientation, and number) are adjusted to minimize the difference between a predicted signal, based on these parameters, and the actual measurements. There is no unique three-dimensional inverse solution for an arbitrary current distribution, given any number of measurements of magnetic field or potentials at or beyond the conducting boundary. This property is a consequence of the Helmholtz reciprocity principal. Consequently, one must apply constraints as to the number and configuration of a finite number of current sources in order to obtain a usable inverse solution. The equivalent current dipole (ECD) model is commonly used to solve the inverse problem from MEG and EEG measurements. In this model, the source currents are constrained to be point-like in nature. The location and orientation parameters of one or more dipole models is adjusted for best fit to the measurements. The equivalent current dipole fit is just one of many prior art inverse solutions that are commonly used with MEG and EEG.

Source estimation is usually based upon application of a spatially selective filter to the MEG and/or EEG measurements. Rather than fitting a model to the measurements, the estimation methods filter is the fraction of the MEG or EEG signal that could have been generated from a specified coordinate in the brain. This requires that signals are measured simultaneously from an array of sensors, and not by serial measurement using one or few sensors that are moved from site to site. An image of brain activity is constructed by applying the filter at each coordinate in the head. The intensity of brain activity that is projected by the filter at each site generates corresponding voxel intensity in a false color map (i.e., the functional image). The SAM method estimates source strength by a process of spatially-selective noise reduction. That is, the correlated measured signal arising from all regions other than the target coordinate are suppressed. Signals arising from source current at the target coordinate are passed by SAM.

Source estimation by SAM is robust in the presence of correlated and uncorrelated noise. As noise increases, the spatial resolution and contrast of the resulting functional image is degraded. By contrast, images derived from inverse solutions tend to degrade abruptly in the presence of small amounts of noise. If the source model used for inverse solution does not account for all sources present (including environmental noise, and errors in determining baseline) then the source locations found will be in error. Inverse solutions generally require very large signal-to-noise ratio, and may rely on signal-averaging to provide this. The SAM method performs source estimation and imaging of spontaneous unaveraged MEG data. The depth resolution of source images computed by SAM may not be adequate for unique three-dimensional source localization. However, differential images and images created by the SSAM method of the present invention both resolve source activity in three dimensions.

(2) Brief Review of Functional Brain Imaging Technology

Prior art functional brain imaging technology differs significantly from the SSAM method of the present invention. All methods except for those using MEG and/or EEG are indirect measures of brain activity. The use of indirect measures has its advantages and disadvantages, as will be discussed.

"Positron emission tomography" (PET) is a technique that images changes in brain metabolism or blood flow. Oxygen, glucose, or any other biochemical substrate that can be labeled by a positron-emitting radioisotope may be used as a tracer. The tracer may be attached to a substrate that will selectively bind to specific cell sites within the body. The tracer is introduced into the subject—either by injection into an artery or by inhalation. The PET camera consists of an array of scintillation detectors that measure the high-energy 511 keV photon pairs (gamma radiation) emitted 180 degrees apart at sites of positron-electron annihilation. Because each event produces a pair of photons, the detectors are designed to take advantage of correlated counts. An image is computed by mapping the sites of positron-electron annihilation. Positron emitting radioisotopes generally have a half-life of only a few minutes. Hence, an accelerator such as a cyclotron must be available on-site for producing the radiopharmaceuticals. A PET scan may not be repeated once the maximum allowable radiation exposure has been reached. PET is therefore considered an invasive technology. PET has limited spatial resolution due to the uncertainty of where annihilation occurs; a positron has a mean free path of several millimeters in brain tissue. Furthermore, PET's response time to changes in brain activity is very slow. The mechanism coupling brain electrophysiological changes to metabolic changes is not rigorously understood. Nonetheless, PET imaging of brain activity has demonstrated important applications in both clinical and basic research of brain function. Because a special facility is required for generating the short-lived radiopharmaceuticals, the cost of PET is very high.

"Single photon emission computed tomography" (SPECT), like PET, is a nuclear medical imaging technique for detecting sites of gamma photon emission in the brain. Unlike PET, the radioisotopes used in SPECT imaging emit a single gamma photon per decay event. The SPECT camera consists of an array of collimated scintillation detectors. Biologically active materials such as pharmaceuticals may be labeled with a gamma-emitting radioisotope such as Technetium 99 m and injected into the subject or patient. The radiotracer may also be introduced as a gas—a radioactive isotope of Xenon, for example. The distribution of the isotope may then be imaged using the SPECT camera. As an example, SPECT (and PET) can image the distribution of the neuroreceptors in the brain to specific neurotransmitters. One can also measure regional changes in cerebral blood flow and volume consequent to changes in brain activity.

"Functional magnetic resonance imaging" (fMRI) is a functional neuroimaging method using much the same hardware as conventional MRI. In addition to imaging the anatomy of the brain, fMRI images contrast changes due to local changes in blood oxygenation, blood flow, or blood volume. Functional MRI therefore provides an indirect measure of brain activity. Like PET and SPECT, it relies upon coupling of electrophysiological activity to metabolic and hemodynamic changes. As a consequence of the slow response time of the coupling mechanisms, fMRI has poor temporal resolution of neurological events. Cognitive fMRI studies require considerable creativity in directing sensory stimuli to the subject, as it is necessary to overcome factors such as high noise levels and small space for the subject's head. Although fMRI can be studied using conventional MRI hardware, better signal-to-noise and resolution are obtained using specialized high-field superconducting magnets, thus raising the instrumentation costs.

"Optical neuroimaging" methods take advantage of changes in light transmission or light scattering at the cortical surface. The localized event-related changes in blood flow and oxygen level giving rise to the fMRI image are observed optically in the exposed brain. Furthermore, it has been shown that electrophysiological events in the brain result in changes in photon scattering. Such changes may be detected transcranially with methods such as "evoked response optical signal" (EROS). The field of optical functional imaging has not yet matured. However, it is likely that it will be limited to mapping the cortical surface of the brain due to the opacity of the brain tissue.

Magnetoencephalography and electroencephalography analysis methods are often categorized as functional imaging techniques. MEG and EEG are both direct measures of the brain's electrophysiological activity. In the case of MEG, sensors are used to detect the time-varying magnetic fields that are generated by the time-varying ionic currents of the electrophysiological processes. EEG, on the other hand, measures the electrical potential differences that are due to the same electrophysiological time-varying ionic currents.

Magnetoencephalographic instruments require extremely sensitive magnetic field detectors. The peak-to-peak magnetic signal strength of brain activity for a typical subject is only approximately one picoTesla ($10^{-12}$ Tesla). By contrast, the magnetic field of the Earth is approximately 50 microTesla ($50 \times 10^{-6}$ Tesla), or 50 million times stronger. In order to detect such weak magnetic signals such as those from the brain, state-of-the-art instruments use a superconducting electronic component called a "dc-SQUID" (acronym for direct-current Superconducting Quantum Interference Device). Each SQUID sensor consists of a superconducting flux transformer that is placed in close proximity to the head, coupled to a dc-SQUID device. Magnetic fields, such as those arising from electrophysiological events, are coupled into the flux transformer where they induce a current that is transformed by the SQUID into a voltage. Room-temperature electronics are used to read out and linearize the SQUID's voltage pattern so as to faithfully reproduce the magnetic field that was induced in the flux transformer. Because the SQUID and its flux transformer are superconducting and operate at temperatures of less than 5.0 degrees Kelvin (i.e., above absolute zero), the SQUID sensor possesses extremely low noise and large dynamic range. The SQUID sensor must be maintained at this low temperature—for example, by a bath of liquid helium. The sensors and liquid helium are contained within a cryogenic dewar so that they are isolated from the subject. At the same time, the dewar must be constructed such that the sensor flux transformers can be as close as possible to the subject's head. In practice, dewars are constructed so that the flux transformer is one to two centimeters from the room temperature surface of the dewar.

In order for the SQUID sensor to faithfully reproduce the brain signal, without interference from the environmental magnetic field fluctuations, it is common to use differentially-wound flux transformers, termed "gradiometers." It is also common to perform MEG measurements within a magnetically-shielded room that is designed to greatly attenuate magnetic interference. The SQUID sensors used by CTF Systems Inc. of Port Coquitlam, British Columbia, Canada digitally synthesize a high-order gradiometer from physical magnetometer and first-order gradiometer sensors. The synthetic high-order gradiometers (i.e., sensors of high-order spatial derivatives of the magnetic field) provide for greatly improved rejection of magnetic interference, such that good quality MEG measurements can be obtained without a magnetically-shielded room.

Modem MEG instruments use a helmet-shaped array of closely-spaced sensors, so that MEG signals from the entire head can be acquired simultaneously. Since the MEG signals are measured without any electrical contact with the subject, no subject or patient preparation, such as attachment of electrodes, is necessary as would be required for EEG measurement. Thus, MEG measurements can be conducted rapidly and efficiently by simply positioning the subject's head within the helmet-shaped SQUID sensor array. An additional benefit of MEG measurement is that it can detect very slowly changing or direct current signals. By contrast, the electrochemical interface of the EEG electrode with the skin may give rise to electrical potentials that contribute to measurement drift and therefore confound very low frequency measurements.

Electroencephalographic instruments are much simpler and are presently less costly than MEG instruments. The electrical potential that result from electrophysiological activity within the brain are measured by placing electrodes on the scalp of the subject and connecting these to sensitive amplifiers. The brain signals are conducted to electrodes in contact with the scalp through multiple layers of tissue (i.e., cerebral cortex, meninges, cerebrospinal fluid, skull and scalp). The electrical potential at points on the scalp is quite small, being on the order of 100 microvolts ($10^{-4}$ volts) or less. Moreover, the variability of the multiple conducting layers makes it difficult to obtain an accurate forward solution for the potentials that would result from the electrophysiological activity. Consequently, inverse solutions based upon EEG measurements, alone, tend to be less accurate than those based upon MEG measurements. EEG measurements using passive electrode technology require conductive electrode paste to provide low impedance electrical contact with the scalp. Application of passive electrodes is slow, requiring marking of proper electrode positions, mild abrasion of the scalp, application of paste and use of tapes and adhesives to affix the electrodes. Because this, preparation of a patient for EEG is time consuming, costly, and often unreliable. MEG has the advantage of providing for a large number of recording sites with no preparation. More recently, so-called "active electrodes" have become available for EEG. The active electrodes consist of a field-effect transistor (FET) that is placed in close-contact with the scalp. The very high input impedance of the FET allows EEG recording without conducting electrode paste. Multiple active electrodes are also available in cap-like arrays that can be fit over the head. This can reduce the time needed to prepare a patient for EEG.

The most common inverse solution used both for MEG and EEG measurements is the equivalent current dipole (ECD) fit. A current dipole is a model that assumes that current is flowing across a point-like element. Given such a model, each ECD can be described by its position and current vectors. For EEG measurements, six parameters are required—three for position and three for orientation. For MEG measurements, only five parameters are required when modeling the magnetic field of a dipole in a homogeneously conducting sphere. That is because the radially directed component of the current does not produce an external magnetic field. If the ECD is oriented radially, the magnetic field of the volume currents will exactly cancel that due to the primary current (the ECD). When realistic (i.e., non-spherical) head geometry is modeled, the radial components of the ECD do give rise to a magnetic field. Therefore, an ECD with six parameters will be used in inverse solution.

Inverse solution for one or more current dipoles is obtained by performing a least-squares fit between the magnetic field and/or electrical potentials predicted by the dipole model and the actual MEG and/or EEG measurements at a particular instant of time. An accurate ECD solution requires high signal-to-noise ratio MEG and/or EEG signals. The presence of noise leads to uncertainty as to the location or orientation of the dipole. In addition, simultaneous solutions for more than a few dipoles tend to be unreliable. This is a consequence of there being a large number of possible dipole configurations that could lead to similar measurements. The presence of noise thus makes it impossible to distinguish a single unique configuration, without use of additional constraining information.

It is common practice to plot the positions (and, sometimes, the orientations) of each ECD on an anatomic image of the brain. This process is sometimes referred to as "magnetic source imaging," or "MSI." The term "MSI" is misleading and inaccurate, as superimposing a marker, representing an ECD solution, onto an MRI image does not constitute functional brain imaging. Legitimate functional brain imaging technologies, such as PET or fMRI, represent brain activation as occurring over a measurable area and possibly multiple locations, in agreement with physiological knowledge. The dipole model is merely a useful hypothetical construct. It does not accurately represent the underlying electrophysiological sources. For example, a dipole fit to epileptic interictal "spike" activity will often appear deeper within the head than it actually is. This is because the "spike" generator is likely to be a cortical surface with an area of several square centimeters. The magnetic field pattern of an extended source is quite similar to that of an equivalent current dipole that is much deeper in the head. The ECD solution, although widely used, may be severely limited in its clinical application.

The minimum-norm solution is a more general approach to inverse solution. In its simplest form, the current sources are modeled as being continuous, everywhere in the head. In more sophisticated models, the current sources are constrained to the cortical surface, using either actual anatomic measurements or a realistic model of the brain. A linear inverse solution based upon both the source model and the MEG and/or EEG measurements, at some instant of time, is used to recover the current distribution that gave rise to the measurements. Such solutions are not unique, due the Helmholtz reciprocity principle. Furthermore, such solutions are underdetermined, as there will always be more possible source parameters than there are measurements. The minimum-norm method will show only one of an infinite number of possible source solutions. Often the minimum-norm solution will be weighted to emphasize deep rather than superficial sources. Nonetheless, the non-uniqueness of such solutions limits its application in functional brain imaging. An image created by application of the minimum-norm solution can also be superimposed and fused with an anatomical image of the brain.

Source estimation can be an extremely useful MEG and EEG analysis technique. The fundamental philosophy of source estimation can be summarized as follows: If one is willing to accept the non-uniqueness of the electromagnetic inverse solution, then one must abandon its requirement of fitting the measurements by a model. Given this principle, then one must seek measures of the likelihood of there being source activity at any particular coordinate in the brain. An exhaustive review of estimation methods and inverse solutions is beyond the scope of this disclosure. The MUSIC method (acronym for "multiple signal classification") localizes sources by partitioning a covariance matrix of the measurements into two subspaces—one containing the signal and the other containing the noise. The signal and noise will be orthogonal at locations for which there was source activity. Orthogonality between the noise subspace and a forward solution (from a model) is tested for each coordinate in the head. Regions where orthogonality is at maximum are assumed the locations of source activity.

The MUSIC method is applicable to data for which there is a distinct transition between signal and noise subspaces. Spontaneous brain signals arise from a very large number of source generators—much larger than the number of sensors used in MEG or EEG measurement. Therefore, there can be no noise subspace. Measurement data that have been signal averaged, such as that from an evoked response study, have a simpler spatial structure, as only those regions of the brain that responded synchronously with the external events can have a non-zero average. In the limit, all regions responding asynchronously will have a zero mean. Signal-averaged data can usually be separated into signal and noise subspaces for MUSIC analysis. However, the signal-averaging requirement limits the usefulness of MUSIC for localizing primary sensory and motor areas of the brain. Higher brain functions are less well synchronized to external events and are therefore attenuated by signal averaging. It should be noted that this characteristic also limits the areas that can be localized by the ECD solution.

Source activity may also be estimated using a spatially selective filter. The principle behind this is relatively simple. The spatial response of any single MEG sensor is usually very broad. That is, any given sensor detects a signal that is the superposition of signals from all generators. The spatial response of a sensor limits its detection to only a general region. It would be desirable if that sensor's response could be limited to only a tiny region of space. If this could be achieved, then the signal it measures would be that due to source activity within its response pattern. Unfortunately, electromagnetic physical laws dictate that response of realizable sensors, no matter how complex, are most sensitive to sources in their vicinity, with sensitivity declining with distance. Measurements made on or near the surface of the head cannot be made more sensitive to sources in the interior of the head than they are to sources that are on the surface. Invasive depth electrodes can be inserted into the brain and record signals from a tiny region containing only a few neurons. Noninvasive measures using MEG or EEG sensors respond to a much larger volume of space.

The so-called "Fourier lens" method projects the MEG and EEG measurements from an array of sensors through a mathematical process that transforms regularly-sampled measurements of field or potential directly into a source image. This method is made more complicated when the sensors are not spaced at regular intervals, which is the case for all commercial MEG instruments. The Fourier lens obeys the reciprocity principle, and therefore can only estimate source currents at the surface of the head. A three-dimensional solution is forbidden, as the sensitivity of MEG or EEG sensors declines with depth into the head.

Lead field synthesis (LFS), as taught by U.S. Pat. Nos. 4,977,896 and 5,269,325 is a method whereby the signals measured by an array of MEG and/or EEG sensors is projected through a spatial filter that is defined by a linear sum of sensor measurements. The output of the filter is a time-series representing an estimate of the source strength of the region that was selected by a set of weighting coefficients.

Synthetic aperture magnetometry (SAM), subject of U.S. Provisional Application No. 60/072,340 filed Jan. 23, 1998, is also a projection method. It requires observation of signal simultaneously from an array of sensors. Unlike LFS, SAM solves for an estimate of the root mean square (RMS) source activity over a specified time window and frequency band. Functional images of RMS source activity are built up by applying the method to discrete locations in space that coincide with the region of interest in the brain. The SAM method does not maximize sensitivity at some point inside the head (which is forbidden by reciprocity). Instead, it minimizes or attenuates the interfering signals that are generated from regions other than the one selected. SAM can be recognized as belonging in a class referred to as a "super-resolution beamformer" (see: B. Widrow and S. D. Steams, "Adaptive Signal Processing, Beamformers with Super-resolution", Prentice-Hall Inc., Englewood Cliffs, N.J., pp. 445–455, 1985). A super-resolution beamformer can exceed the maximum resolution dictated by the reciprocity principle by selectively attenuating interfering sources. The response of the beamformed array only appears to be very selective. In reality, its spatial response will be quite complex and will be dictated by the signals that are present. The SAM method makes use of sensor noise to obtain an optimal Backus-Gilbert tradeoff of noise and resolution, under conditions where sensitivity to the source is low. Radio telescopes and radar antenna arrays make use of super-resolution beamforming to provide high resolution images of radio sources or radar targets. Unlike the Fourier lens, SAM is able to resolve sources in three dimensions.

(ii) The SSAM Invention
(1) Mathematical Approach to Synthetic Aperture Magnetometry Since the SSAM method of the present invention is an extension of the SAM method, it is convenient to review the mathematical foundations of the SAM method before discussing the SSAM method. Both the SAM and SSAM methods may be applied to MEG data, EEG data, or a simultaneous combination of the two. In all cases, measurements from all sensor locations must be sampled simultaneously. The method does not apply to serial measurements for which a sensor or sensors are moved from place to place. Since the method applies to an array of sensors, one may denote the measurement of all sensors by M and the measurement of the $i^{th}$ sensor by $m_i$. The symbol M denotes the total number of sensors, and K denotes the total number of time samples. Hence, the measurement data are represented by a two dimensional matrix:

$$M = \begin{bmatrix} m_{11} & m_{21} & m_{31} & \cdots & m_{M1} \\ m_{12} & m_{22} & m_{32} & \cdots & m_{M2} \\ m_{13} & m_{23} & m_{33} & \cdots & m_{M3} \\ \vdots & \vdots & \vdots & \ddots & \vdots \\ m_{1K} & m_{2K} & m_{3K} & \cdots & m_{MK} \end{bmatrix}. \quad (1\text{-}1)$$

In a similar fashion, the distribution of sensitivity throughout the measurement space is denoted by a Green's function G, and that of an individual sensor by $G_i$. The vector arrow above the symbol for individual sensors denotes that the Green's function is itself a vector quantity:

$$G = \vec{G}_1, \vec{G}_2, \vec{G}_3, \ldots, \vec{G}_M. \quad (1\text{-}2)$$

The Green's functions provide a generalized representation of the sensitivity patterns of either MEG or EEG sensors. In order to solve the Green's function for a given sensor type, one substitutes the appropriate forward solution. For example, one might use the forward solution by Sarvas (magnetic field due to a current dipole in a homogeneously conducting sphere; see Sarvas, J. (1987), "Basic mathematical and electromagnetic concepts of the biomagnetic inverse problem," Phys. Med. Biol. 32:11–22) to represent the Green's function of a MEG sensor. A forward solution is used here to denote a mathematical solution predicting the magnetic field at a sensor or electrical potential difference between two or more electrodes, given the position and vector of currents within a specified conducting space having specified boundaries and conductivity. Given this definition, the measurement value of the $i^{th}$ sensor to a current distribution J at time sample k, within conducting volume $\Omega$ is:

$$m_{ik} = \int_\Omega J(r) \cdot \vec{G}_i(r) dr^3, \quad (1\text{-}3)$$

where r denotes the coordinate vector within conducting space $\Omega$. Integration is over the entire volume $\Omega$—for example, the head or brain.

The current J represents the electrical (or, rather, ionic) source currents that are generated by the electrophysiological activity of nerve cells within the brain (or any electrically active tissue within the body). Since J is a vector quantity, one must specify both position and direction vectors for the source current. The symbol $\theta$ is used here to denote a particular target within the head:

$$\theta = r, u \quad (1\text{-}4)$$

where u is a unit vector in the direction of the source current flow at coordinate r.

Accepting the possibility, implied by equation [1-3], that there may be current flowing everywhere in the head, there will consequently be no unique solution. However, one can observe the magnetic fields and electrical potentials generated by this current at multiple measurement sites, simultaneously. The instantaneous source strength S at $\theta$ for time sample k can therefore be estimated (denoted by the carat above the S) by some linear combination of the simultaneous sensor measurements:

$$\hat{S}_{\theta k} = W_\theta^T M_k. \quad (1\text{-}5)$$

The time dimension is required for the estimation of weighting coefficients, since the measurements at any time sample may result from the superposition of a large number of sources and sensor noise. Observation of those measurements over a number of samples is required to resolve the superpositions. In the SAM approach, one solves for the weighting coefficients W that minimize the total signal power; this is the squared value of the source estimate:

$$F(W_0) = \sum_{k=1}^{K} \hat{S}_{\theta k}^2 \quad (1\text{-}6)$$

$$= \sum_{k=1}^{K} [W_\theta^T M_k]^2,$$

$$= W_\theta^T R W_\theta$$

where R is the correlation matrix, for which each element is defined as:

$$R_{ij} = \frac{1}{K} \sum_{k=1}^{K} m_{ik} m_{jk} \quad (i, j = 1, 2, 3, \ldots, M). \quad (1\text{-}7)$$

The integration is computed for K discrete time samples. Integration can also be performed using any selected combination of samples. These do not necessarily have to be in any order, or continuity. The correlation matrix is the time integral of the products of measurements from each sensor by every other sensor. For example, using measurements from a MEG instrument having 151 sensor channels could yield a correlation matrix of up to 151 by 151 elements.

The dc-SQUID (superconducting quantum interference device) is presently the most sensitive device for detecting the magnetic fields of the brain and other organs. MEG measurements made using dc-SQUID sensors can contain an unknown dc-offset or baseline. As a consequence of this, one can substitute the covariance matrix C for the correlation matrix R in equation [1-6]:

$$F(W_\theta) = W_\theta^T C W_\theta. \quad (1\text{-}8)$$

The covariance is identical to the correlation, except for removal of the mean measurement value (the unknown baseline). This is:

$$C_{ij} = \frac{1}{K} \sum_{k=1}^{K} [m_{ik} - \overline{m}_i][m_{jk} - \overline{m}_j], \quad (1\text{-}9a)$$

where the mean measurement is computed in the conventional manner:

$$\overline{m}_i = \frac{1}{K} \sum_{k=1}^{K} m_{ik}. \quad (1\text{-}9b)$$

In addition to the correlated behavior of the MEG or EEG measurements, one must also account for the uncorrelated noise. This noise does not refer to environmental or biological forms of interference, but rather specifies the instrumentation noise. When using state-of-the-art dc-SQUID sensors, this is primarily the SQUID noise level. The measurement noise variance (for all sensors) is denoted by a diagonal matrix $\Sigma$ in which the individual sensors are denoted by $\sigma^2$:

$$\Sigma = \begin{bmatrix} \sigma_1^2 & & & & \\ & \sigma_2^2 & & 0 & \\ & & \sigma_3^2 & & \\ & 0 & & \ddots & \\ & & & & \sigma_M^2 \end{bmatrix}. \quad (1\text{-}10)$$

Function F in equation [1-6] is a measure of source power, as it is the squared source estimate. It is interpreted as the total power projected by the weighting coefficients W for target $\theta$; this will be evident, later, following derivation of the weights. Since the measured signal includes uncorrelated noise, the source power estimate will be the sum of the signal and noise powers. The correlated portion of the measurement is due to source activity within the brain, along with biological and environmental noise signals. The uncorrelated portion of the measurement is entirely due to instrumental noise such as SQUID noise, Johnson noise from local normal conductors such as RF shields, and noise in room temperature electronics.

The estimated source noise variance that is projected by the weighted linear combination of measurements is given by:

$$\sigma_\theta^2 = W_\theta^T \Sigma W_\theta. \quad (1\text{-}11)$$

This gives the statistical noise that would appear in a time-series projection from equation [1-5]. The instantaneous (sample) noise, of course, cannot be predicted. Nonetheless, the noise power (over a designated period of time) can be determined and removed from the source estimate. The noise directly affects the achievable spatial resolution of the SAM method. As will be shown, the weighting coefficients are derived from the covariance matrix.

According to mathematical theory first explored by Backus and Gilbert (see Parker, R. L. (1977), "Understanding inverse theory," Ann. Rev. Earth. Planet. Sci. 5: 35–64), a solution or estimate of a source will itself contain errors due to the noise of the measurement. The relationship between how well one can solve for the locus of activity and how accurate the solution value is, forms a sort of "uncertainty principle" known as the Backus-Gilbert trade-off. As this relates to MEG or EEG measurements, if one attempts to form a linear combination (equation [1-5]) that estimates brain source activity with the highest possible spatial resolution, one must accept a corresponding error or noise in that estimate. If one chooses to reduce the spatial selectivity, one can then reduce the noise of the estimate. However, in reducing spatial selectivity, one can no longer be certain that the source estimate at some coordinate is not contaminated by activity from some other part of the brain. Hence, in this synthetic aperture approach to estimating source power due to brain activity, it is necessary to set the lower limit of error or noise in the estimate, such that this error does not exceed the resolution for which one desires to know the source strength. For example, to estimate brain activity, one might set the upper limit of noise to $1 \times 10^{-9}$ Ampere-meters root mean square (RMS). Thus, source activity exceeding this value could be resolved.

The Backus-Gilbert trade-off becomes important when estimating source strength for sources that are distant from the sensors. This is because the Green's functions of MEG and EEG sensors decline as a power of distance from the source currents. Since sensitivity declines, the noise level of the source estimate must increase with distance. One can compensate for this by setting a lower limit of noise. That is:

$$W_\theta^T \Sigma W_\theta \leq \xi^2. \quad (1\text{-}12)$$

One then solves for the weighting coefficients by minimizing the function indicated by equations [1-6] or [1-8], subject to the noise constraint of equation [1-12] and a gain constraint (the gain constraint of equation [1-13] transforms the measurement units (magnetic field, in Tesla, or electrical potential, in Volts), which are dependent upon distance between the target and the sensors, to source strength (dipole moment, in Ampere-meters), which is independent of the target-sensor spacing) implying that there is unity gain for the source estimate, regardless of distance from the sensor array:

$$W_\theta^T G_\theta = 1. \quad (1\text{-}13)$$

The linear weights are found by solving:

$$F(W_\theta) = W_\theta^T C W_\theta . \min . W_{s.t.} W_\theta^T C W_\theta \leq \xi^2 \text{ and } W_\theta^T G_\theta = 1 \quad (1\text{-}14)$$

This yields the constrained minimum variance solution:

$$W_\theta = \frac{[C + \mu \Sigma]^{-1} G_\theta}{G_\theta^T [C + \mu \Sigma]^{-1} G_\theta}, \quad (1\text{-}15)$$

where $\mu$ is the regularization parameter. When $\mu$ is zero, equation [1-15] reduces to:

$$W_\theta = \frac{C^{-1} G_\theta}{G_\theta^T C^{-1} G_\theta} \quad (\mu = 0). \quad (1\text{-}16)$$

When $\mu$ is infinity, equation [1-15] becomes:

$$W_\theta = \frac{G_\theta}{G_\theta^T G_\theta} \quad (\mu = \infty). \quad (1\text{-}17)$$

The regularization parameter $\mu$ is actually bounded between minus one and infinity. The highest spatial selectivity is achieved when $\mu$ is minus one, representing the condition in which sensor noise variance is removed from the diagonal elements of the covariance. Negative values of $\mu$ should be used with caution, as noise fluctuations present in the off-diagonal covariance elements can lead to degenerate solutions.

Weights are not required to estimate source activity. Recognizing that function F in equation [1-8] is actually the mean square source plus noise power, one has (dropping the caret above S):

$$S_\theta^2 = W_\theta^T C W_\theta. \quad (1\text{-}18)$$

This equation may be rewritten without the weighting coefficients as:

$$S_\theta^2 = [G_\theta^T (C + \mu \Sigma)^{-1} G_\theta]^{-1}. \quad (1\text{-}19)$$

2) Subtractive Imaging Using Synthetic Aperture Magnetometry

The foregoing discussion summarizes the SAM method, as disclosed in U.S. Provisional Application No. 60/072,340 filed Jan. 23, 1998. In that disclosure, difference imaging was shown to be the best mode for SAM. That is, one computes two covariance matrices from MEG measurement data segments delineating so called "active" and "control" brain states. Two volumetric images are then created from each of two covariance matrices by estimating source strength at specified intervals over a three-dimensional grid of points (i.e., the volume elements, or "voxels"). A voxel-by-voxel subtraction of functional images of an active state "a" and a control state "c" yields a third image representing the difference in source power between the two states:

$$^{(a-c)}S_\theta^2 = {}^{(a)}S_\theta^2 - {}^{(c)}S_\theta^2. \tag{2-1}$$

The effect of this subtractive process is to remove common-mode brain signals which are unrelated to the conditions used to induce the active and control states. Yet another reason for the subtraction is that the individual maps represent the signal plus noise for each voxel, and not the signal, alone. As discussed earlier, the sensitivity of the sensors declines with distance. Hence, the strength of the RMS source plus noise increases proportionally. At the center of electrical symmetry for the brain (near its center), the sensitivity of MEG sensors declines to zero. Consequently, the noise fraction of the source estimate rises to infinity. In fact, a non-subtractive image of brain activity, created with this embodiment of the SAM method, will appear to grow progressively "brighter" (in a false-color representation) toward the interior of the head; this tends to obscure the fluctuations in brain activity so that they are not readily visible in the images. The subtractive imaging process removes the common-mode noise as well as the common-mode brain source activity. This tends to reduce, but not eliminate, the influence of the image noise increase as a function of depth. Some noise remains in the difference image, because the random noise for the two states may not be the same.

(3) Rationale and Mathematical Basis for SSAM: Statistical Imaging

The present invention, SSAM, overcomes many of the limitations of the SAM method. The primary limitation of the SAM method is that the source strength estimate tends to grow progressively larger toward the center of the head (i.e., the center of the volume conducting space). This problem is quite evident when imaging brain activity without background subtraction. It is less evident when computing difference images (subtraction of background brain activity). The sources of brain activity are normally found by searching for peaks or maximum values in the functional images. The overestimation of source intensity with depth in SAM images makes sources tend to appear deeper within the head than they actually are.

The SSAM method overcomes the problem of poor depth resolution. This is accomplished by displaying estimates derived from the source strength-to-noise ratio, instead of the source strength, alone. The rationale for this improvement may be explained, as follows. SAM is related to a class of adaptive array processing referred to as a "constrained minimum variance beamformer". The instrumental noise projected by such a beamformer is smallest under two conditions. First, noise is small when the voxel being estimated is distant from other sources of correlated signal. Second, it is also small when the voxel coincides precisely with an active source. Noise increases in regions where sources are "cluttered" close to one another, and increases when estimating activity immediately adjacent to an active region (although there may be no source in the voxel location). This increase in noise results from the minimum variance beamformer trying to minimize the signal power "leaking" through from the adjacent source. The beamformer adapts to this condition by increasing spatial selectivity to reject more of the adjacent source power. However, as indicated by the Backus-Gilbert relationship, this increase in selectivity has a corresponding increased noise penalty. Of course, one can use the regularization factor $\mu$ to reduce the projected noise of the estimate. However, this will increase the signal power "leaking" through from the adjacent source, thus reducing resolution (which may be forced to fall to unacceptable levels).

Since the resulting SAM image (formed by application of equation [1-19] to each voxel) does not discriminate between source strength and noise, it will appear to have very low spatial resolution and contrast. However, one can still account for the fluctuations in noise, by sing equation [1-11]. The source-strength-to-noise ratio can be computed using the expression:

$$z_\theta = \left[ \frac{S_\theta^2 - \sigma_\theta^2}{\sigma_\theta^2} \right]^{1/2}. \tag{3-1}$$

The symbol z, which is used to denote the SAM SNR, is equivalent to the z-statistic for the voxel. Images or functional maps that are derived from source statistics are commonly used in positron emission tomography (PET) or functional magnetic resonance imaging (fMRI). The process of mapping a statistical image is referred to conventionally as "statistical parametric mapping" or "SPM." Equation [3-1] represents a means of creating an SPM{z} image of functional brain activity from MEG, EEG, or both.

It should be noted here that equation [3-1] does not merely represent a trivial conversion of mapping units from source strength (Ampere-meters) to a corresponding statistic. The reduction of noise effects on the functional image will have a profound effect on source image resolution and contrast. This improvement over the previous embodiment of SAM will be demonstrated by example.

In a similar manner, a differential image may be formed after accounting for and reducing the effects of the uncorrelated noise. The Student's T-statistic, which is related to the source difference-to-noise ratio between active state "a" and control state "c" is given by the equation:

$$^{(a-c)}T_\theta = \left[ \frac{n|{}^{(a)}S_\theta^2 - {}^{(c)}S_\theta^2|}{{}^{(a)}\sigma_\theta^2 + {}^{(c)}\sigma_\theta^2} \right]^{1/2}, \tag{3-2}$$

where the averaged RMS noise is computed using equation [1-11], using the combined noise variance of the active and control states, and n is the number of trials.

Images created using equation [3-2] are referred to as SPM{t} images. The SPM{t} image from equation [3-2], improves over the previously disclosed SAM method by accounting for the fluctuations in noise resulting from the properties of the SAM minimum variance beamformer. The resulting source statistical difference images have higher spatial resolution and higher contrast than the original embodiment.

Those skilled in the art will be further assisted in comprehending the SSAM method of the present invention by a more rigorous derivation of the noise estimate appearing in the denominators of equation [3-2]. To this point, only the uncorrelated noise due to the instrumentation has been considered. In fact, one can also take into consideration the image noise arising from random fluctuations of the active and control state measurements. The null hypothesis addressed by the T-statistic is, "Could the difference between the active and control states have arisen by chance?" To answer this, one must examine the intrinsic variability of the measurement data used to derive the active and control states. In other words, can randomly selected active and control state data produce the same voxel T-values as did the selected data?

Consider a difference imaging study in which measurements are divided up into multiple time windows representing the instances of control and active states of brain activity. For the purpose of this discussion, assume that there are n trials, each containing an active and a control state time segment. One derives the covariance matrices of either the active or control states using equation [1-9] by summation over all samples for the respective states. The summation over the trials can also be rewritten as:

$$^{(a)}C_{ij} = \frac{1}{n}\sum_{e=1}^{n} {}^{(a)}C_{ij}(e) \qquad (3\text{-}3)$$

$$^{(c)}C_{ij} = \frac{1}{n}\sum_{e=1}^{n} {}^{(c)}C_{ij}(e).$$

If there were n instances of control and n instances of the active state, the respective covariance matrices would then be computed by integration over all samples of all instances for their respective states. However, one can postulate that any difference between the active and control state covariance matrices may have arisen by chance alone. To test this hypothesis, one can form two additional covariance matrices from a random combination of the active and control state data. The example given, using odd and even trial combinations is not representative of a random combination of events. Equation [3-4] is presented merely to be instructive as to methods for estimating experimental measurement noise. One could also have used a random number generator to select the data used for integration into matrix and . The odd and even trial method will work, provided that there is no deterministic effects of trial number on brain activity. Instead of labeling them "a" or "c" for active and control, respectively, the two hybrid covariance matrices are denoted as "α" and "β." For example, one can compute one covariance matrix by integrating data using even numbered control trials summed with odd numbered active trials (trial index denoted by "e"):

$$^{(\alpha)}C_{ij} = \frac{1}{n}\sum_{e=1}^{n} \begin{Bmatrix} \text{even } e & {}^{(a)}C_{ij}(e) \\ \text{odd } e & {}^{(c)}C_{ij}(e) \end{Bmatrix} \qquad (3\text{-}4)$$

$$^{(\beta)}C_{ij} = \frac{1}{n}\sum_{e=1}^{n} \begin{Bmatrix} \text{even } e & {}^{(c)}C_{ij}(e) \\ \text{odd } e & {}^{(a)}C_{ij}(e) \end{Bmatrix}.$$

The second covariance matrix is computed using odd numbered control trials and even numbered active trials. From the two "mixed-state" covariance matrices, one computes two additional volumetric images, using equation [1-19]. The absolute value of the voxel-by-voxel difference between these two images is a measure of the variability of the data used to generate the true control and active state images. The total noise variance is the sum of that due to instrumental noise and that from the data variability:

$$\sigma_\theta^2(\text{total}) = {}^{(a)}\sigma_\theta^2 + {}^{(c)}\sigma_\theta^2 + |{}^{(\alpha)}S_\theta^2 + {}^{(\beta)}S_\theta^2|. \qquad (3\text{-}5)$$

By substituting equation [3-5] for the noise (denominator) in equation [3-2], one obtains:

$$^{(a-c)}T_\theta = \left[ \frac{n|{}^{(a)}S_\theta^2 - {}^{(c)}S_\theta^2|}{{}^{(a)}\sigma_\theta^2 + {}^{(c)}\sigma_\theta^2 + |{}^{(\alpha)}S_\theta^2 - {}^{(\beta)}S_\theta^2|} \right]^{1/2}. \qquad (3\text{-}6)$$

The Student's T-statistic of equation [3-6] will accurately account for both instrumental noise and experimental reliability. The precise manner in which the experimental variability is accounted for will depend upon the design of the measurement study; equation [3-6] is given only to show an example of its incorporation into the measurement statistics. Both the z and T-statistics of each voxel may be reduced further to its corresponding probability value (p-statistic). Other differential image comparisons could be computed, including those combining more than two states of brain activity. The basis upon which the T-statistic or other statistics are computed can be reformulated, depending upon the new combination of states.

Computation of functional brain images from MEG, using the z-statistic of equation [3-1] or the accurate T-statistic of equation [3-6], is not a trivial change in units from RMS dipole moment (or differential moment) to their corresponding statistical measures. Instead, the improvement is based upon the observation that the magnitude of the RMS dipole moment increases as a function of depth in the head. This increase results primarily from the increase in uncorrelated noise rather than from an increase in source moment. One can compensate for this property by plotting the source signal-to-noise ratio (SNR). As a result, one observes that higher resolution and image contrast can be obtained by mapping the SNR of the source power estimate rather than the power itself. The z and T-statistics may be thought of as measures of SNR. The resulting functional images represent a significant improvement over preceding methods. The SSAM method is accordingly capable of revealing details of brain activity that were previously hidden.

(4) Step-by-Step Procedures for Computing Functional Images with the SSAM Methods A step-by-step procedure for computing functional brain images from MEG measurements, using the SSAM method is now provided. This section will detail the SSAM computations from the original MEG data to the final functional images of various statistical types. The mathematical notation used is identical to that used in the previous sections.

(a) Imaging Single-State of Brain Activity by SSAM

Step 1: Multichannel MEG data signals (without signal averaging) is collected. The data streams are preferably 20 seconds or longer in duration, and preferably 64 or more MEG sensor channels are used.

Step 2: The MEG data is preferably filtered in a frequency domain, defining the range of frequencies of interest. These could be conventional frequency bands—for example, alpha-frequency (8 to 13 Hz)—or user-defined frequencies that emphasize brain activity features such as epileptic spikes, abnormal low frequency waves, and so on. Filtering is not required if all brain source frequencies are of interest.

Step 3: MEG data are selected from a sample time window or windows that emphasize particular intervals of brain activity. For example, one might select times during which the subject is engaged in reading, doing mathematics, listening to music, or during bursts of abnormal activity such as epileptic interictal spikes. The time samples that are selected need not be contiguous. However, the total time selected is preferably greater than 20 seconds. If all MEG data are of interest, then the time window will include all data samples.

Step 4: The covariance or correlation matrices are computed from the selected data. The covariance matrix is preferred, as MEG measurements may have an unknown baseline (DC-offset). The offset will have little effect on SSAM functional images when using a large number of sensors. Nonetheless, one degree of freedom will be lost if an offset is present on any or all channels. Hence, it is preferred that the covariance be computed rather than the correlation matrix. Each element of the covariance is computed using the equation[5]:

$$C_{ij} = \frac{1}{K}\sum_{k=1}^{K}[m_{ik} - \overline{m}_i][m_{jk} - \overline{m}_j] \quad (4\text{-}1)$$

There are a variety of computational methods for estimating the covariance or correlation matrix. Equation [4-1] is presented as one example. This does not exclude other methods.

Step 5: Select an array or grid of points ("voxels") defining a region of interest. For example, the voxels could be arranged in a regular equidistant Cartesian three-dimensional grid encompassing the entire head. The voxels could also be arranged over a curvilinear surface—for example, one defining the surface of the cerebral cortex. Note that, although the array of points is determined by their position r, the unit current vector u must eventually be specified or computed. This is because SAM exhibits selectivity to all elements of the target parameter θ.

Step 6: Determine or compute the uncorrelated noise variance (for the same bandwidth as was used for computing the covariance) for each sensor. This can be accomplished using spectral decomposition of the MEG measurements—for example, by means of a Fourier transform. Alternatively, one can estimate the sensor noise variance from the covariance matrix, itself. First, apply an eigendecomposition such as a singular value decomposition (SVD) to the covariance matrix. Every matrix C can be expressed as a product of three submatrices such that:

$$C = USV^T, \quad (4\text{-}2)$$

where U and V are both orthogonal matrices representing the spatial modes of C (see Golub, Gene H. and Van Loan, Charles F. 1983, Matrix Computations, Baltimore, Johns Hopkins University Press). Submatrix S is a diagonal matrix of the singular values of C. Assuming that the measurement units are Tesla, the singular values will have units of Tesla². Each singular value represents the signal power for each element of the SVD. The singular values can be sorted in order of decreasing magnitude. One selects the least significant singular value to represent the sensor noise variance:

$$\Sigma = s_M I \quad (4\text{-}3)$$

This procedure may overestimate the average sensor noise variance, but is usually more accurate than a Fourier transform on the MEG data, since the presence of brain signals may mask the sensor noise. The SVD of the covariance matrix is advantageous, as it not only provides an upper limit of the sensor noise variance, but also can be used to simplify subsequent computations of weighting coefficients and source power.

Step 7: Compute weighting coefficients for each target voxel—with or without Backus-Gilbert tradeoff (no tradeoff if $\mu=0$):

$$W_\theta = \frac{[C+\mu\Sigma]^{-1}G_\theta}{G_\theta^T[C+\mu\Sigma]^{-1}G_\theta}. \quad (4\text{-}4)$$

Step 8: For each voxel at target θ, compute the mean-square source moment (referred to here as "source power") or (optionally), with or without Backus-Gilbert tradeoff of noise and spatial resolution:

$$S_\theta^2 = [G_\theta^T(C+\mu\Sigma)^{-1}G_{74}]^{-1} \quad (4\text{-}5)$$

The symbol G denotes the Green's functions for the sensor array. The Green's function allows computation of the response of the sensors to a point-like current element flowing at the target. Equation [4-3] requires specification of the optimal current vector u for each target coordinate r. The preferred method for finding u is from the unit normal vector to the surface of the cortex. This may be extracted from measurement of an anatomical image of the brain such as from a MRI or CT scan. An alternative approach is to find the current vector u that maximizes the source power. The search for the vector at which source power is at a maximum can be performed efficiently by a successive approximation algorithm. (Equation [4-5] appears in the denominator of equation [4-4]. Hence, the source power can be computed most efficiently as a step in computing the weighting coefficients.)

Step 9: For each voxel, compute the noise variance using the identical value of θ as was used for the corresponding voxel source power.

$$\sigma_\theta^2 = W_\theta^T \Sigma W_\theta \quad (4\text{-}6)$$

Step 10: Optionally, one can derive a "corrected" estimate of the source power of each voxel by subtracting the estimated noise variance for that voxel. This corrected source power should be interpreted as a useful oversimplification (the process of linear noise subtraction is, in fact, an oversimplification; SAM minimizes signal power (variance) for each voxel, and can minimize some of the instrumental noise as well as signal; as a result, SAM will give an accurate estimate of source strength at locations where there are concentrations of source power B even when the noise estimate is quite large):

$$S'^2_\theta = S_\theta^2 - \sigma_\theta^2. \quad (4\text{-}7)$$

Step 11: Compute the source power to noise variance ratio (SNR), which is either:

$$\rho_\theta = \frac{S_\theta^2}{\sigma_\theta^2}, \quad (4\text{-}9a)$$

or (optionally), with noise subtraction:

$$\rho'_\theta = \frac{S'^2_\theta}{\sigma_\theta^2} \quad (4\text{-}9b)$$

$$= \frac{S_\theta^2 - \sigma_\theta^2}{\sigma_\theta^2}.$$

The voxel value may be represented either directly by ρ or by its square root. The square root of the SNR may be thought of as a z-statistic, as it represents the ratio of a measurement to its standard deviation. In the following statistical examples, it is understood that the SNR be computed either with or without noise subtraction:

$$z_\theta = [\rho_\theta]^{1/2}. \qquad (4\text{-}9c)$$

Step 12: Optionally, convert the z-statistic into a corresponding probability (p-value), using the appropriate statistical distribution.

Step 13: Convert the values obtained by equation [4-9], or its p-value into a false-color or gray-scale image of source activity. The z-statistic and its related arithmetic quantities are used in forming images of brain activity without differential comparisons. It is therefore useful for imaging epileptic, migraine, and other types of spontaneous brain activity.

Step 14: Coregister the SSAM functional image with an anatomical image such as from MRI or CT scan, and display the fused anatomic and functional image data.

Figure 2:
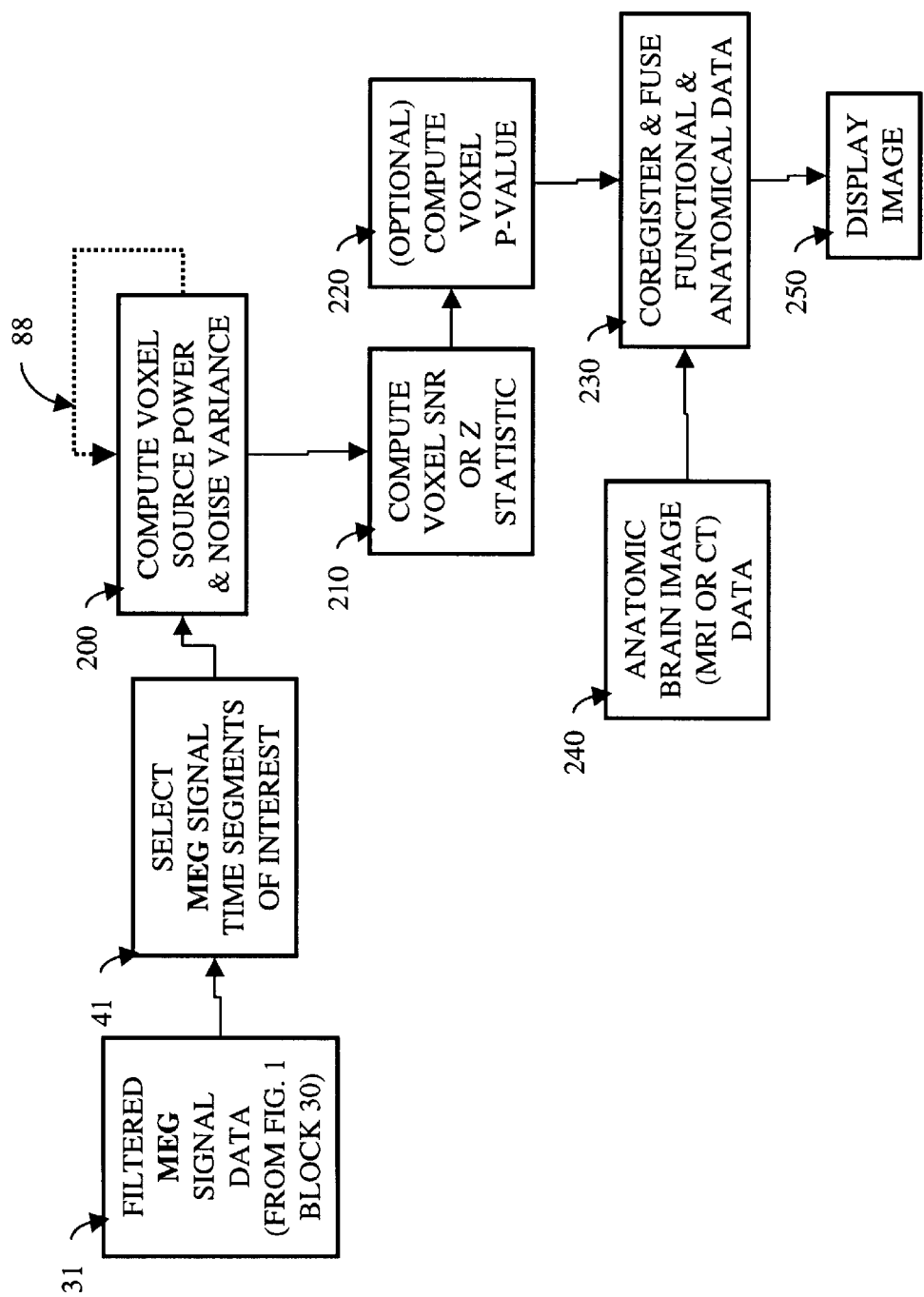
FIG. 2 is a flowchart which depicts the preferred sequence of steps for deriving functional images with only one state of brain activity being measured (i.e. images are made without background subtraction using a control state).
Figure 3:
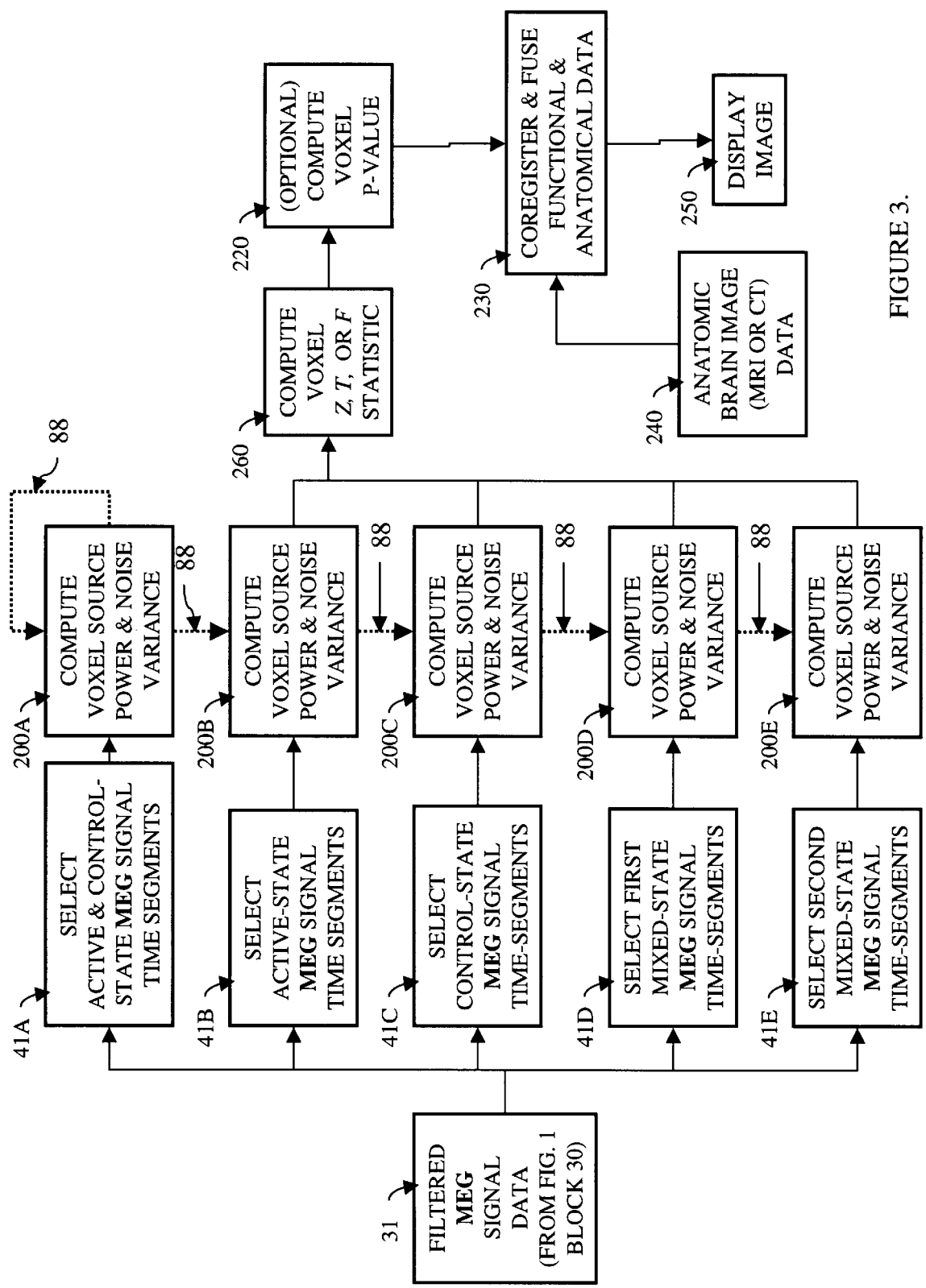
FIG. 3 is a flowchart which depicts a sequence of steps for deriving functional images with both active and control states of brain activity being measured.

To further assist those skilled in the art in comprehending the invention, the following the foregoing steps are now reviewed in relation to flowchart FIGS. 1–3. As indicated in FIG. 1, block 10, magnetoencephalographic measurements 10, comprised of MEG signal data 12 and sensor position data 14 representative of the sensors' positions relative to the brain, are collected. A frequency specification 20 is selected to emphasize specific frequencies of brain activity (or all frequencies are selected, as required). A bandpass filtration step 30 is then performed on MEG signal data 12, utilizing the selected frequency specification 20, and well known digital or analog filtration technology.

A time segment (or segments) 40 is specified to emphasize specific activities or states of brain activity (or one may choose to select the entire signal record, if required). As indicated at block 50, the filtered MEG signal data and the time segment specification are then used to compute a covariance matrix 50 in accordance with equation 4-1 or other suitable mathematical methods for estimation of signal covariance, as known in the art. The filtered MEG signal data is also used to compute a noise variance matrix (block 60) in accordance with equations 4-2 and 4-3, or other suitable mathematical methods for estimation of signal uncorrelated noise variance, as known in the art.

A list 70 of voxel coordinates defining the region of interest and resolution (voxel spacing) for determination of a functional image is selected. For each voxel in list 70, a target voxel specification 80, comprised of a voxel position vector 82 and a voxel current vector 84, is determined. Voxel current vector 84 may be determined from anatomic data incorporated into voxel list 70, or may be determined iteratively by maximizing the source power as indicated at 88. In the latter case, voxel current vector 84 may be initialized with a guess. A forward solution is then computed (block 90) using voxel target specification 80 and sensor position data 14. Forward solutions are known to the art (for example, see the previously cited Sarvas reference). The forward solution is denoted by a Green's function G, to generalize to solutions for magnetic field or electrical potentials in a variety of known conducting geometries. Synthetic aperture magnetometry (SAM) beamforming coefficients (weights) are then computed using equation 4-4, as indicated at block 100.

The voxel source power can now be derived (block 110) with the aid of equation 4-5, or from the SAM weights, using equation 1-18. In practice, solution of equation 4-4 may be used as one mathematical step in solving for the weights. If voxel current vector 84 is not known from anatomic data 86, then voxel current vector 84 is adjusted to maximize voxel source power, as indicated at 112. The voxel source noise variance is derived (block 120) using equation 4-6. The steps corresponding to blocks 70 through 112 are repeated for all voxels in voxel list 70. The voxel source power and voxel noise variance are combined to form statistical quantities as will now be explained with reference to FIGS. 2 and 3.

With reference to FIG. 2, block 31, filtered magnetoencephalographic signal data is obtained as previously explained in relation to FIG. 1, block 30. Time segments defining the occurrences of brain activity of interest are then selected (block 41). Voxel source power and source noise variance are then computed (block 200) as previously explained with reference to blocks 50 through 120 of FIG. 1. The current orientation vector for each voxel may be determined, optionally, by maximizing source power as indicated at 88. Determination of this vector from anatomical data (the vector normal to the cortical surface) is preferred. In the absence of anatomic vector data, iterative maximization of power is preferred.

As indicated at block 210, the voxel source power to noise variance ratio, or z-statistic can then be computed using equations 4-9a, 4-9b, or 4-9c. Optionally, as shown at 220, a probability value can be determined for each voxel, using distribution functions well known in the statistical arts.

The functional and anatomic image data is then combined, as shown at 230 (i.e. the functional image, comprising the previously derived array of voxels, is coregistered and fused with corresponding voxels defined by a separately provided anatomic image 240). Coregistration assures that the coordinates of each of the voxels of the functional image coincide with the coordinates of the voxels defining the anatomic image. The functional and anatomic images are then fused into a single image. For example, the combined images can be represented as the sum of a two color and gray scale image. Alternately, only the statistically significant portions of the functional image may be rendered as opaque, allowing the anatomical image to be visible in regions where the functional image is not statistically significant. Varying degrees of transparency and thresholding may be employed to represent the coregistered functional and anatomical images as a single fused image, in accordance with display methods which are well known to persons skilled in the functional brain imaging art. The combined image is then displayed as indicated at 250.

The foregoing steps show how to compute a functional brain image, without subtraction of background brain activity. When data are available for background (also called "common-mode" or "control-state") brain activity, functional images can be derived from the comparisons of two or more states of activity. The following steps illustrate quantities that are useful for functional brain imaging when comparing an active and control state.

(b) Imaging Two or More States of Brain Activity by SSAM: Ratio of Active & Control Steps 1 through 11 (from above): Compute source power to source noise variance ratio ($\rho$) for active and control state time windows, using separate covariance matrices. The time window, described above in step 3, defines the segments of time (from the measurement data) having the brain activity of interest. Using the conventional definition, the active time window implies a time during which the subject or patient is performing some task involving sensory input, motor output, or engaged in specific cognitive activity such as reading or speaking. The control state time window selects measurement data reflecting background brain activity, during which the subject is performing a background "control" task. Ideally, the control interval should differ only for the one condition being studied for the active condition. The measurements for each state are obtained preferably by segmenting a single set of measurement data, so that there is no need to compensate for movement of the head position relative to the sensors. Detailed information respecting the experimental design of a functional brain imaging study can be found in the scientific literature on functional imaging for PET and fMRI studies.

Step 12: A useful method for generating a functional image comparing active and control states is to compute the signal-to-noise ratio (equation [4-9]) for the active and control states, forming the ratio of ratios:

$$^{(a:c)}\eta_\theta = \frac{^{(a)}\rho_\theta}{^{(c)}\rho_\theta}. \tag{4-10}$$

The ratio is computed independently for each voxel. The prefix "(a)" and "(c)" denotes the active and control states, respectively. It is preferable for the current vector u to be identical for solutions of the active and control state voxels. This can be accomplished either by deriving u from anatomical data, or by maximizing source power for one or the other state. One can also find u by maximizing source power for a third covariance matrix made up of the sum of the active and control state covariance matrices.

The ratio of active and control signal-to-noise ratios from equation [4-10] has the same form as the familiar F-statistic. That is, it represents a ratio of measurement variances. This functional image derived from this ratio can then be fused with an anatomic image, as was indicated in steps 9 and 10. A probability value can be computed for each voxel. The expected value of $\eta$ is 1.0, assuming the null hypothesis postulating that there is no difference between the active and control states. One can plot $\eta-1$, for which positive values indicate greater signal-to-noise ratio for the active state, and negative values indicate greater signal-to-noise ratio for the control state.

Each voxel can be represented as a gray-scale or false color image that can be fused with anatomical image data, as discussed previously, and displayed.

More particularly, as shown in FIG. 3, multiple segments of MEG data can be utilized to compare two or more states of brain activity. To accomplish this, filtered magnetoencephalographic signal data is again obtained (block 31) as previously explained in relation to FIG. 1, block 30. As indicated at blocks 41A through 41E, time segments defining the individual and combined occurrences of both active and control state brain activity of interest are selected.

Specifically, filtered active plus control magnetoencephalographic signal data is selected (block 41A) and the active plus control voxel source power and source noise variance are then computed (200A) as previously described with reference to blocks 50 through 120 of FIG. 1. Optionally, the current orientation vector for each voxel may be determined by maximizing the source power 88. A current vector may also be determined from any of the other time segments. Determination of this vector from anatomical data (the vector normal to the cortical surface) is preferred. As previously indicated, in the absence of anatomic vector data, it is preferable to maximize power iteratively, in which case it is again preferable to determine the vector from the combined active and control states, since that will best represent a single vector for all conditions.

As indicated at block 41B, filtered time segments defining the occurrences of active state brain activity of interest are selected. The active-state voxel source power and source noise variance are then computed (block 200B), as previously described with reference to blocks 50 through 120 of FIG. 1, with the current vector being optionally obtained (block 88) for each voxel as previously explained. Time segments defining the occurrences of control state brain activity of interest are selected (block 41C) and the control-state voxel source power and source noise variance are computed (200C) as previously described with reference to blocks 50 through 120 of FIG. 1, with the current vector being optionally obtained (block 88) for each voxel as previously explained. Time segments defining the occurrences of the first mixed state brain activity of interest are selected (block 41D), using equation 4-11. The first mixed-state voxel source power and source noise variance are then computed (block 200D) as previously described with reference to blocks 50 through 120 of FIG. 1, with the current vector being optionally obtained (block 88) for each voxel as previously explained. Time segments defining the occurrences of the second mixed state brain activity of interest are selected (block 41E), using equation 4-11. The second mixed-state voxel source power and source noise variance are then computed (block 200E) as previously described with reference to blocks 50 through 120 of FIG. 1, with the current vector again being optionally obtained (block 88) for each voxel as previously explained.

As indicated at block 260, voxel z-statistic, T-statistic, or F-statistics are computed, using equations 4-14 and 4-15 (as examples of computing the z-statistic), equations 3-2 or 3-6 (as examples of computing the T-statistic), or equation 4-13 (as an example of computing the F-statistic). Optionally, a probability value is determined (block 220) for each voxel, using statistical distribution functions well known to those skilled in the statistical mathematics art.

The functional and anatomic images are then combined (block 230). The functional image, comprising the previously derived array of voxels is coregistered with voxels defining a separately provided anatomic image (block 240). The functional and anatomic images are then fused as aforesaid and the combined image is then displayed (block 250).

(c) Accounting for Measurement Variability in Comparisons of Active & Control States The value of $\eta$ from equation [4-10] might be above or below 1.0 by chance alone, due to lack of reliability of the measurement data. A more sensitive test of significance should ask if the value of $\eta$ could occur by chance, alone. To test this, one must determine what value of $\eta$ could occur by chance from the measurements. As was shown for the T-test, one can compute two additional covariance matrices—designated "($\alpha$)" and "($\beta$)"—that each have random content of both active and control state measurements:

$$^{(\alpha)}C_{ij} = \frac{1}{n}\sum_{e=1}^{n}\begin{Bmatrix} \text{even } e & ^{(a)}C_{ij}(e) \\ \text{odd } e & ^{(c)}C_{ij}(e) \end{Bmatrix} \tag{4-11}$$

$$^{(\beta)}C_{ij} = \frac{1}{n}\sum_{e=1}^{n}\begin{Bmatrix} \text{even } e & ^{(c)}C_{ij}(e) \\ \text{odd } e & ^{(a)}C_{ij}(e) \end{Bmatrix}.$$

One can then express the ratio of the two mixed states in the same manner as that for active and control:

$$^{(\alpha:\beta)}\eta_\theta = \frac{^{(\alpha)}\rho_\theta}{^{(\beta)}\rho_\theta}. \tag{4-12}$$

Deviation of this quantity from the expected value of 1.0 will be a consequence of the variability of the measurement, and unrelated to the conditions designated as active and control. The active vs. control ratio can then be compared with the "α" vs. "β" ratio in an F-test by computing:

$$^{(a:c)}F_\theta = \frac{\begin{cases} \text{if } \eta \geq 1 & ^{(a:c)}\eta_\theta - 1 \\ \text{if } \eta < 1 & 1 - ^{(a:c)}\eta_\theta^{-1} \end{cases}}{\begin{cases} \text{if } \eta \geq 1 & |^{(a:\beta)}\eta_\theta - 1| \\ \text{if } \eta < 1 & |1 - ^{(a:\beta)}\eta_\theta^{-1}| \end{cases}}. \quad (4\text{-}13)$$

As was noted previously, the ratio η has a skewed distribution, with an expected value of 1.0 (for large N). The above equation converts the distribution of η into a symmetric distribution with a mean value of zero. Equation [4-13] may appear odd, as it is a ratio of ratio of ratios! However, this equation legitimately represents an F-statistic for any particular voxel, taking into account the variability of the experimental data. As before, each voxel can be represented as a gray-scale or false color image that can be fused with anatomical image data and displayed.

Better statistical reliability can be achieved by deriving a higher-order statistic describing the fluctuations of the "α" to "β" ratio (equation [4-12]) over multiple voxels. As an example, one could take the V voxels neighboring the voxel of interest, and compute the standard deviation of η. In the limit, one could measure the fluctuations over all voxels. The standard deviation, in either case, is computed using:

$$^{(a:\beta)}\sigma = \left[ \frac{\sum_{\theta=1}^{V} \left[ \begin{matrix} \text{if } \eta \geq 1 & ^{(a:\beta)}\eta_\theta - 1 \\ \text{if } \eta < 1 & 1 - ^{(a:\beta)}\eta_\theta^{-1} \end{matrix} \right]^2}{V-1} \right]^{1/2}. \quad (4\text{-}14)$$

The ratio of η to its standard deviation should then follow a z-distribution:

$$^{(a:c)}z_\theta = \frac{\begin{cases} \text{if } \eta \geq 1 & ^{(a:c)}\eta_\theta - 1 \\ \text{if } \eta < 1 & 1 - ^{(a:c)}\eta_\theta^{-1} \end{cases}}{^{(a:\beta)}\sigma}. \quad (4\text{-}15)$$

The z-value of each voxel or its corresponding p-value can be represented as a gray-scale or false color image that can be fused with anatomical image data and displayed. A probability value may then be computed for each voxel from the corresponding z, T, or F-statistics, using standard statistical procedures for computing p-values from other statistical quantities (for example, Beyer, William E., "CRC Handbook of tables for Probability and Statistics", The Chemical Rubber Company, Cleveland, 1996). The p-value can then be fused with an anatomical image for display. It is often useful to threshold the functional image, thereby displaying only source activity that is determined to have statistical significance.

(iii) SSAM Reduction to Practice

The operation and effectiveness of SSAM has been tested using both experimental and simulated MEG data. In the following sections, the principles of SSAM are illustrated using images derived from source power, source noise variance, z-statistics, and thresholded p-values. Next, two examples are presented to demonstrate the effectiveness of SSAM in clinical and basic neuroscience studies. The first study, analysis of MEG epilepsy data, illustrates SSAM functional imaging of pathological brain activity without background subtraction. The second study, analysis of MEG data from a study of language, illustrates SSAM functional imaging of higher cognitive brain function by comparison of active and control states.

(1) Demonstration of SSAM Principles and Source Resolution Improvement

Figure 4:
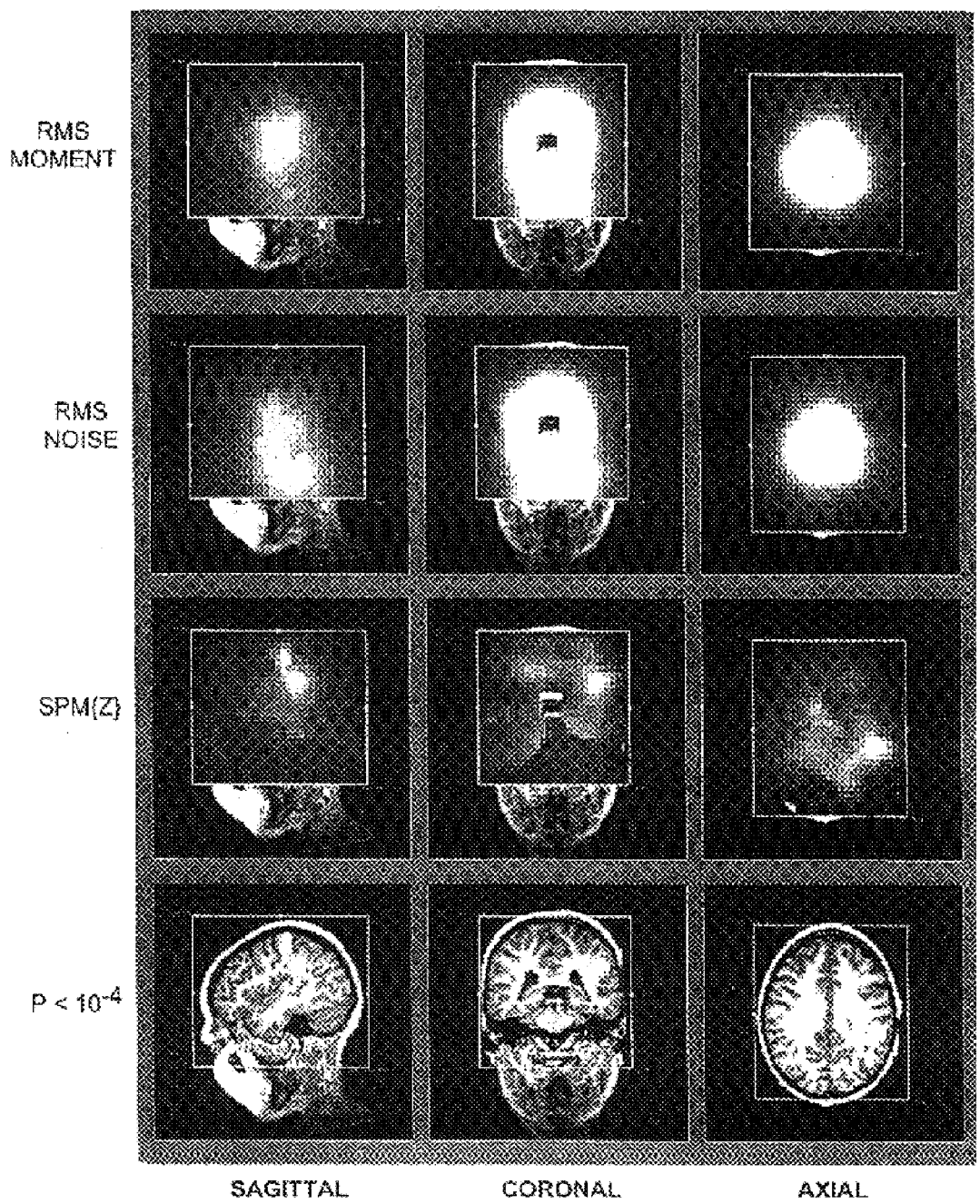
FIG. 4 is a series of images derived from an MEG recording of epileptic brain activity. Three orthogonal views of the brain, labeled "sagittal," "coronal," and "axial" are shown for each image type.

The principles and effectiveness of SSAM are demonstrated by comparing functional images of quantities representing steps in the imaging process. A series of images were derived from an MEG recording of epileptic brain activity, as shown in FIG. 4. Three orthogonal views of the brain, labeled "sagittal," "coronal," and "axial" are shown for each image type. These images provide a perspective view on how image intensity is distributed in a portion of three-dimensional space. The image data are shown superimposed on the subject's MRI. The data collection and processing were identical to the epilepsy data example discussed below—except for generation of intermediate images.

The first row of FIG. 4 shows images of the root mean-square source power, derived by taking the square root of equation 4-5 at each voxel coordinate. The images are adjusted so that all three views use the same intensity scale. Although the RMS source power distribution is evident in the sagittal view, the image intensity is seen to grow progressively stronger toward the center of the head in both the coronal and axial views. Without common-mode background subtraction, as taught by U.S. Provisional Application No. 60/072,340, the RMS source power image does not adequately resolve source activity in three dimensions. Since the subject's brain activity is abnormal, there is no simple way of deriving a matching "control" measurement when brain activity is normal. Hence, one must seek means of improving the image, without background subtraction.

The RMS source noise variance image, shown in the second row of FIG. 4, is derived from the same data as the source power data. It is derived from taking the square root of equation 4-6, computed at each voxel. The spatial pattern of the noise distribution appears to have a similar pattern to the RMS source power. The ability to discern structure in these images has been lost to the general trend of increasing strength toward the interior of the head.

The z-statistic image, derived from application of equation 4-9c, is shown in the third row of FIG. 4. These images exemplify SSAM imaging without common-mode background subtraction. It can be seen that the z-statistic images no longer grow progressively brighter toward the center of the head. Instead, they reveal several regions where the z-statistic forms peaks in three-dimensional space. These images illustrate the fundamental principle of SSAM. Functions that are derived from a ratio of source power and source noise variance reveal significant source activity in three dimensions.

The last row of FIG. 4 illustrates transformation of the z-statistic images into corresponding probability values. The probability values were thresholded at $P<10^{-4}$. That is, the SSAM voxels shown have a very small probability of having occurred by chance. Conversely, it is likely that these voxels circumscribe regions of statistically significant brain activity. In this example, that activity shows the location of regions of epileptic brain activity.

(2) Epilepsy

Figure 6:
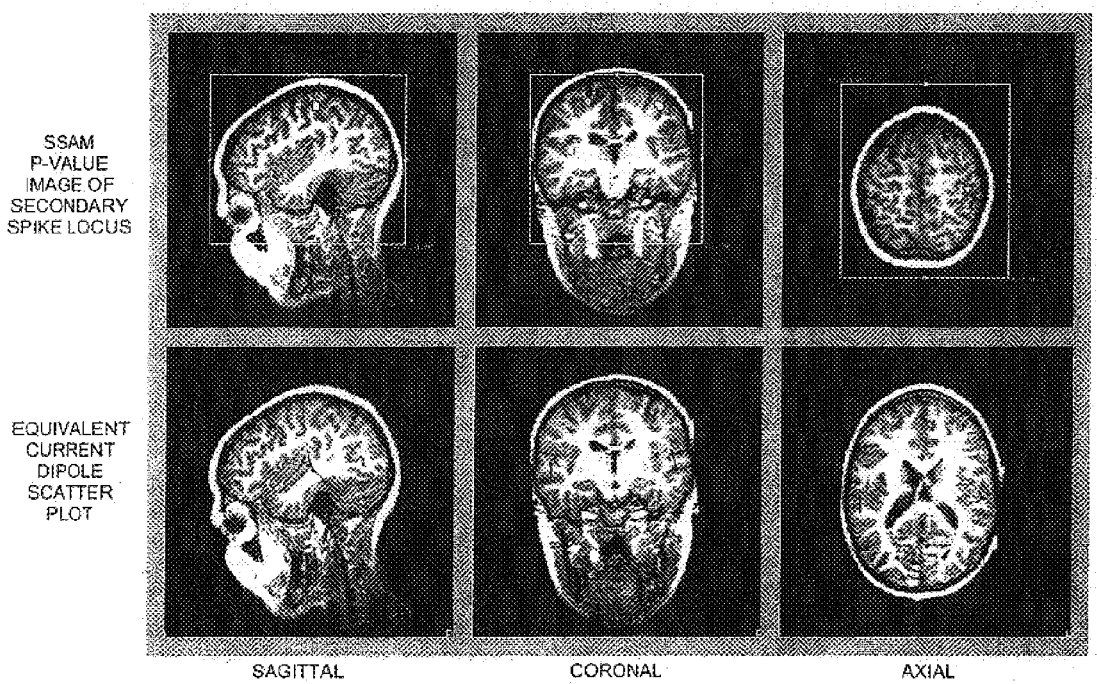
Figure 7:
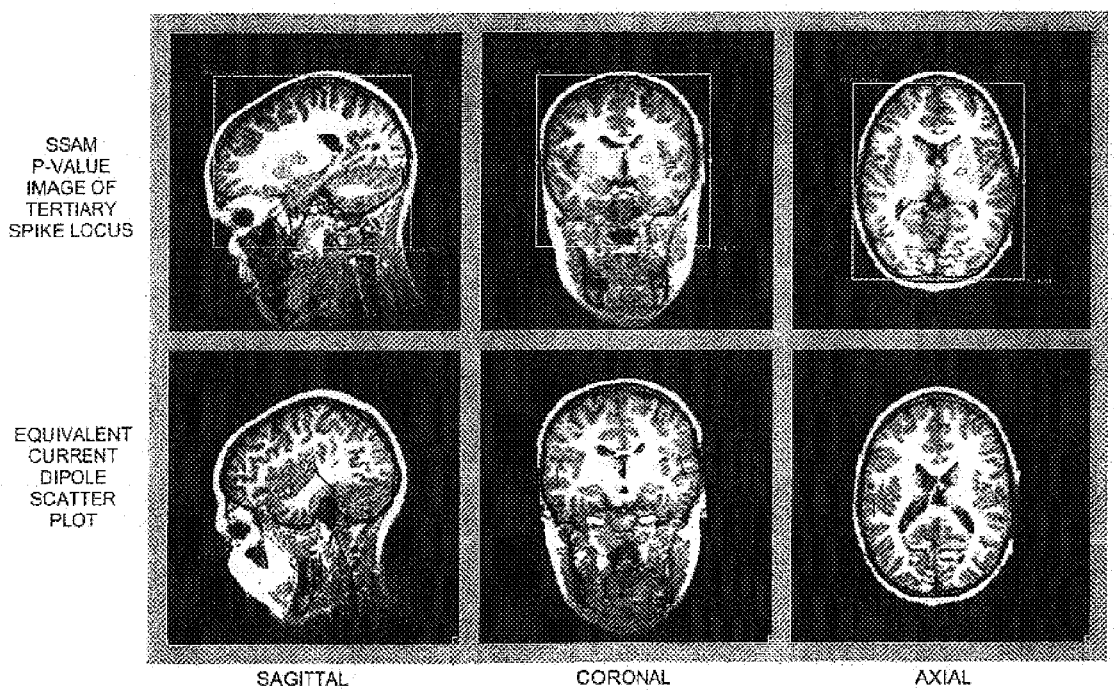

The brain signals of a presurgical epilepsy patient were measured using a 151-channel whole-head MEG instrument. Multiple data sets of 100 seconds, each, were digitized at 625 Hz and stored on disk. Examination of the MEG time series revealed multiple interictal spikes—high amplitude sharp waves—that are characteristic of this patient's type of epilepsy. Epilepsy data were analyzed using two different methods—equivalent current dipole (ECD) fit, and SSAM. The conventional dipole fit method required the painstaking steps of identifying each individual spike, filtering and baseline removal, computation of the dipole coordinate for each sample describing each spike, and finding the earliest reliable ECD fit for each spike. The spike coordinates were then registered with the patient's MRI and plotted as markers on the MRI, in order to show the anatomical origin of the spikes. As shown in the bottom row of FIGS. 5, 6, and 7, spikes localized by ECD appear to be clustered in one region at the posterior margin of the right Sylvian fissure.

The identical epilepsy MEG data that were used to compute the ECD coordinates was analyzed by SSAM, as follows. First, the data were filtered with a bandpass of 25 to 150 Hz. This filter was used to attenuate the signals from the dominant spontaneous brain rhythms, and emphasize the high frequencies associated with interictal spikes. Next, a covariance matrix was computed using the entire 100 seconds of data, of each data set. That is, it was unnecessary to mark or identify the instances of interictal spikes. The covariance matrix was further processed (equation [4-3]) to estimate the uncorrelated sensor noise. A region of interest bounding the entire head was selected, with a Cartesian grid of coordinates at 2.5 mm intervals. SSAM then was used to generate a z-statistic value at each of the coordinates, within the region of interest. The SSAM image was registered with the MRI image, using fiduciary points on the head that were determined identically for the MEG and MRI measurements. The SSAM functional brain image revealed three regions of the brain for which the z-statistic was largest. These were: 1) right central sulcus near the posterior margin of the Sylvian fissure, 2) right central sulcus, at its lateral mid-point, and 3) right posterior thalamus. Regions of large z-values indicate the locations of brain activity that are distinct from the background brain activity.

Figure 5:
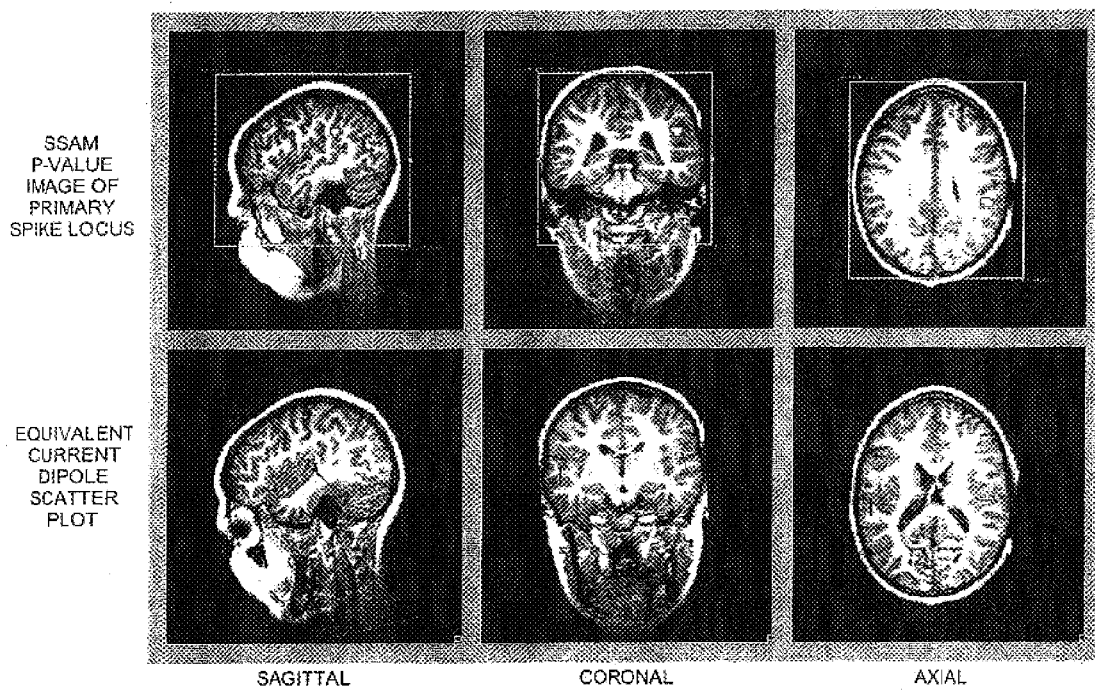
FIGS. 5–7 compare results obtained by the prior art equivalent current dipole methodology (lower row of images in each Figure) with results obtained by the SSAM method of the present invention (upper row of images in each Figure).

The ECD results were then compared with the SSAM results. SSAM identified three regions which appear to be spike generators. The ECD identified only one locus for spike activity. The center of the scatter plot of ECD loci was over one centimeter anterior and inferior to the nearest region identified by SSAM, as shown in FIG. 5. Only one point in the ECD scatter plot corresponded to that of the second site identified by SSAM, shown in FIG. 6. ECD was unable to identify a thalamic source, which appears in the top row of FIG. 7. It is well known that more than four square centimeters of cortex must be activated in order for an interictal spike to be visible above the background brain signals. It follows, then, that the ECD will not accurately localize the site where the spike activity began, but rather the center of the area that has been active when the spike amplitude is high. Furthermore, the magnetic field pattern of an extended source is generally not distinguishable from that of a much deeper dipole source. The accuracy of the SSAM method has been tested using simulated data. The SSAM method can discriminate between compact (i.e., highly dipolar) and extended sources. Interictal spikes usually are initiated by a small portion of the cortex. The MEG signals from the spike "initiators" will be weak but highly dipolar. Hence, the regions identified by SSAM appear to correctly represent regions of abnormal spiking activity. If intraoperative recordings of brain signals confirm the SSAM findings, then MEG and SSAM can be used to provide noninvasive preoperative diagnostics for epilepsy cases.

(3) Language

Figure 8:
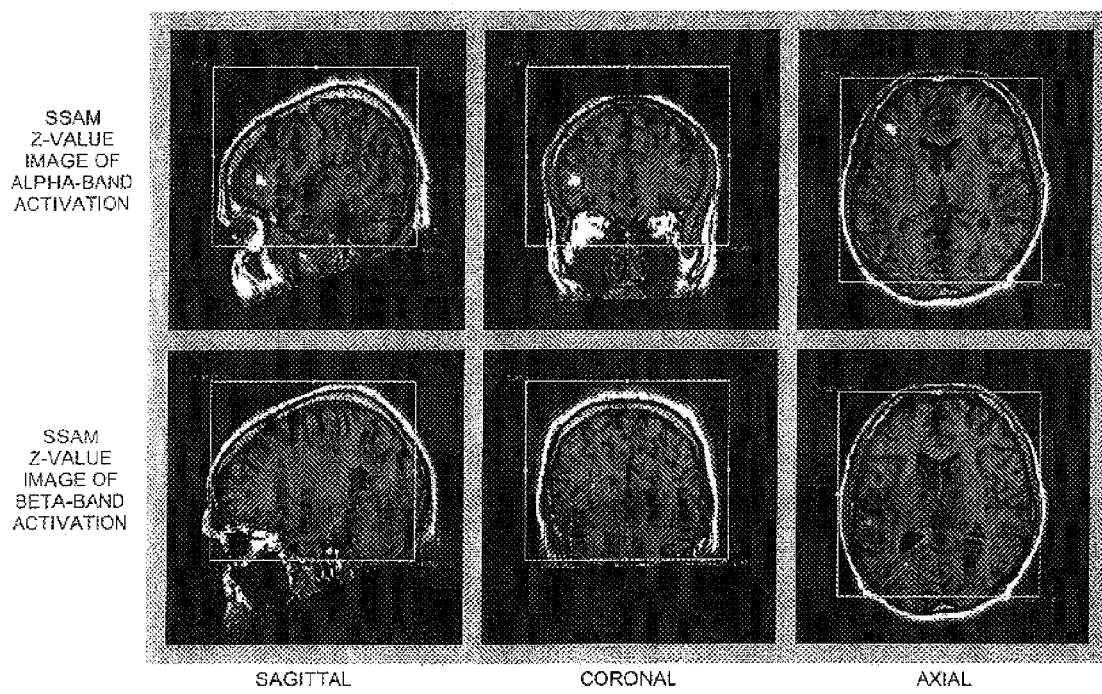
FIG. 8 provides α-band (upper row) and β-band (lower row) functional images of MEG data from an object-naming study having active and control states analyzed in accordance with the SSAM method of the present invention.

SSAM was used to analyze MEG data from an object-naming study. In this study, images of 120 common objects were displayed, one at a time, on an LCD screen. The subject was instructed to watch the LCD monitor and name each object as quickly as possible. MEG data were collected during this task using a 143-channel whole-cortex MEG instrument. The MEG signals were digitized at a 625 Hz rate and saved to hard disk for later analysis. The MEG data were collected as a series of 120 three-second trials. A microphone was used to record the subject's verbal response, and the voice signal was used to generate a digital trigger to mark the onset of vocalization. Each three-second trial began 1.0 seconds prior to the voice trigger and ended 2.0 seconds after the trigger. The MEG data were filtered in a bandpass used to emphasize $\alpha$-band activity (8 to 15 Hz). Next, time segments for an active and a control state were designated, relative to the vocalization-onset trigger. The active state was designated as from 0.5 to 0 seconds prior to the trigger. This interval encompasses the time during which the subject sees the object, retrieves the name of the object from verbal memory, and prepares to speak the name. The control state was designated as 1.0 to 2.0 seconds following the trigger. During this time period, the image of the object remained on the screen, and the subject was merely waiting for the next object to appear. Since 120 trials were used, there were 120 control time segments and 120 active time segments extracted from the MEG data. Five covariance matrices were computed from combinations of the active and control data segments. The first covariance matrix was computed by time integration over both active and control segments. A second covariance matrix was computed by time integration over the active segments, only. A third covariance matrix was computed by time integration over the control segments, only. A fourth covariance matrix was computed from a fifty percent random mix of active and control segments. A fifth covariance matrix was computed for the remaining random active and control MEG data segments. The sensor uncorrelated noise variance was determined for each of the covariance matrices, using singular value decomposition. A region of interest bounding the entire head was selected, using a Cartesian grid of coordinates spaced at 2.5 mm intervals. SSAM was used to generate an z-statistic value for each of the voxel coordinates in the region of interest. The voxel values were then converted into a false colour image which was registered with the coordinates of the subject's MRI image, using fiduciary points on the head that were common to the MEG and MRI measurements. The two images were then fused so that the SSAM image revealed the fluctuations in z-value as a function of anatomical structures in the MRI. The $\alpha$-band functional images are shown at the top row of FIG. 8. The above process was repeated using identical processing, except for filtering the MEG signals to emphasize the $\beta$-band frequencies (15 to 25 Hz). The $\beta$-band image are shown on the bottom row of FIG. 8. Both sets of images are shown in three orthogonal views to illustrate that the regions of activation appear unambiguously in three dimensions. The images made in the two frequency bands emphasize different varieties of source activity. This factor was well-known in EEG studies using topographic (surface) mapping techniques.

Examination of the functional images from this object-naming study revealed activations (i.e., regions for which the z-value was high) in the left hemisphere at sites corresponding to Broca's area and Wernicke's area. These two brain regions are generally believed to be involved in productive and receptive speech, respectively. Several other regions of brain activation could also be identified by SSAM, including areas involved in visual processing of the object images, and sensory and motor cortex for the mouth. None of these areas could be identified or localized using conventional MEG analysis such as signal averaging and dipole fit, because the signals due to higher cognitive activity of the brain is not well synchronized to external events. The MEG SSAM functional images were comparable to those obtained from similar studies using PET or fMRI. This object-naming pilot study marked the first time that MEG had been successful in identifying hemispheric dominance in a language task. It may be useful for clinical determination of hemispheric dominance for language and other higher brain functions, for patients who are to undergo neurosurgery. The SSAM method also can be used as a completely noninvasive basic research tool for studying normal and abnormal brain function.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of making a functional image of a subject's brain from magnetoencephalographic measurements, said method comprising the steps of:

(a) simultaneously collecting a plurality of magnetoencephalographic data signals from a plurality of sensors surrounding said brain;

(b) selecting an array of voxels relative to said plurality of sensors, said voxels defining a region of interest within said brain;

(c) determining one of a correlation matrix and a covariance matrix for said data signals;

(d) determining an uncorrelated noise variance matrix for said sensors;

(e) determining, for each of said sensors, a predicted signal value attributable to a theoretical source of unit strength at each of said voxels;

(f) determining, for each of said voxels, by inverse solution of said matrices and said predicted signal values, a source power, being the mean-square source current dipole moment;

(g) determining, for each of said voxels, an uncorrelated noise variance;

(h) determining, for each of said voxels, a function of said voxel source power and said voxel uncorrelated noise variance;

(i) for each of said voxels, converting said function into a false-color or gray-scale functional image of source activity;

(j) coregistering said functional image with a predefined anatomical image; and, (k) displaying said coregistered images.

2. A method as defined in claim 1, further comprising after said step 1(a), frequency domain filtering said collected magnetoencephalographic data signals to exclude therefrom signal frequencies outside a selected frequency range.

3. A method as defined in claim 2, wherein said selected frequency range is characteristic of a selected brain activity.

4. A method as defined in claim 1, further comprising after said step 1(b), selecting time segmented portions of said magnetoencephalographic signals.

5. A method as defined in claim 4, wherein said time segmented portions are characteristic of a selected brain activity.

6. A method as defined in claim 1, wherein said array of voxels are distributed over a curvilinear surface having a shape conforming to the shape of said subject's cerebral cortex.

7. A method as defined in claim 1, wherein said array of voxels are distributed over a regular equidistant Cartesian three-dimensional grid encompassing said subject's head.

8. A method as defined in claim 1, wherein said step 1(d) further comprises eigendecomposition of said one of said correlation matrix and said covariance matrix.

9. A method as defined in claim 1, further comprising, after said step 1(g), deriving a corrected estimate of said source power by subtracting said uncorrelated noise variance from said mean-square source current dipole moment, for each of said voxels.

10. A method as defined in claim 1, further comprising determining a z-statistic representation of said function.

11. A method as defined in claim 10, wherein said z-statistic representation is a square root of said function.

12. A method as defined in claim 1, further comprising the steps of:

(a) performing said steps 1(a) through 1(h) to determine an active source power to noise variance ratio $^{(a)}\rho_\theta$ while said brain performs an activity task;

(b) performing said steps 1(a) through 1(h) to determine a control source power to noise variance ratio $^{(c)}\rho_\eta$ while said brain performs a control task;

(c) for each of said voxels, deriving a ratio of said active and control source power to noise variance ratios:

$$^{(a:c)}\eta_\theta = \frac{^{(a)}\rho_\theta}{^{(c)}\rho_\theta};$$

(d) converting said ratio of said active and control source power to noise variance ratios into a false-color or gray-scale functional image of source activity;

(e) coregistering said functional image with a predefined anatomical image; and, (f) displaying said coregistered images.

13. A method as defined in claim 1, further comprising the steps of:

(a) performing said steps 1(a) through 1(h) to determine an active source power and an active noise variance while said brain performs an activity task;

(b) performing said steps 1(a) through 1(h) to determine a control source power and a control noise variance while said brain performs a control task;

(c) for each of said voxels, deriving a function containing the ratio of the difference between said active and control source powers to the sum of their noise variance ratios:

$$^{(a-c)}T_\theta = \left[ \frac{n|^{(a)}S_\theta^2 - ^{(c)}S_\theta^2|}{^{(a)}\sigma_\theta^2 + ^{(c)}\sigma_\theta^2} \right]^{1/2} ;$$

(d) converting said function containing said ratio into a false-color or gray-scale functional image of source activity;

(e) coregistering said functional image with a predefined anatomical image; and, (f) displaying said coregistered images.

14. A method of making a functional image of a subject's brain from magnetoencephalographic measurements, said method comprising the steps of:

(a) simultaneously collecting a plurality of magnetoencephalographic data signals from a plurality of M sensors surrounding said subject's brain;

(b) selecting K time-sampled portions of said collected magnetoencephalographic data signals;

(c) deriving a covariance matrix C of elements $C_{ij}$, where:

(i)
$$C_{ij} = \frac{1}{K}\sum_{k=1}^{K}[m_{ik} - \overline{m}_i][m_{jk} - \overline{m}_j];$$

(ii) i,j=1,2,3, ..., M;
(iii) k=1,2,3, ..., K;
(iv) $m_{ik}$ is the response of the $i^{th}$ sensor during time sample k;
(v) $m_{jk}$ is the response of the $j^{th}$ sensor during time sample k;
(vi)
$$\overline{m}_i = \frac{1}{K}\sum_{k=1}^{K} m_{ik} \text{ and } \overline{m}_j = \frac{1}{K}\sum_{k=1}^{K} m_{jk};$$

(d) selecting an array of voxels defining a region of interest within said brain;

(e) determining an uncorrelated noise variance value for each of said sensors;

(f) determining a weighting coefficient
$$W_\theta = \frac{[C+\mu\Sigma]^{-1} G_\theta}{G_\theta^T [C+\mu\Sigma]^{-1} G_\theta}$$

for each of said voxels, where G is Green's function, $\mu$ is a regularization parameter, and T denotes the matrix transpose;

(g) determining, for each of said voxels, at a selected target $\theta$, the mean-square source moment $S_\theta^2 = [G_\theta^T (C+\mu\Sigma)^{-1} G_\theta]^{-1}$;

(h) determining, for each of said voxels, at said respective targets $\theta$, a noise variance $\sigma_\theta^2 = W_\theta^T \Sigma W_\theta$;

(i) determining a function of source power and said noise variance for each of said voxels;

(j) converting said function into a false-color or gray-scale functional image of source activity;

(k) coregistering said functional image with a predefined anatomical image; and, (l) displaying said coregistered images.

15. A method as defined in claim 14, further comprising before said step 14(b), frequency domain filtering said collected magnetoencephalographic data signals to exclude therefrom signal frequencies outside a selected frequency range.

16. A method as defined in claim 15, wherein said selected frequency range is characteristic of a selected brain activity.

17. A method as defined in claim 14, wherein said selecting step 14(b) further comprises selecting time segmented portions of said magnetoencephalographic signals.

18. A method as defined in claim 17, wherein said time segmented portions are characteristic of a selected brain activity.

19. A method as defined in claim 14, wherein $M \geq 64$.

20. A method as defined in claim 14, wherein said array of voxels are distributed over a curvilinear surface having a shape conforming to the shape of said subject's cerebral cortex.

21. A method as defined in claim 14, wherein said array of voxels are distributed over a regular equidistant Cartesian three-dimensional grid encompassing said subject's head.

22. A method as defined in claim 14, wherein said step 14(e) further comprises eigendecomposition of said covariance matrix.

23. A method as defined in claim 14, wherein said step 14(e) further comprises applying an eigendecomposition $C=USV^T$ to said covariance matrix C, where S is a matrix of singular values representing signal power for each of the spatial modes of C, and U and V are orthogonal matrices containing spatial modes of C.

24. A method as defined in claim 14, wherein said function is a ratio determined as
$$\rho_\theta = \frac{S_\theta^2}{\sigma_\theta^2}.$$

25. A method as defined in claim 24, further comprising, after said step 14(h), deriving a corrected estimate of source power by subtracting said noise variance from said mean-square source moment, for each of said voxels.

26. A method as defined in claim 25, further comprising determining a z-statistic representation of said function.

27. A method as defined in claim 26, wherein said z-statistic representation is $z_\theta = [\rho_\theta]^{1/2}$.

28. A method as defined in claim 14, further comprising the steps of:

(a) performing said steps 14(a) through 14(h) to determine an active source power to noise variance ratio $^{(a)}\rho_\theta$ while said subject's brain performs an activity task;

(b) performing said steps 14(a) through 14(h) to determine a control source power to noise variance ratio $^{(c)}\rho_\theta$ while said subject's brain performs a control task;

(c) for each of said voxels, deriving a ratio of said active and control source power to noise variance ratios:
$$^{(a:c)}\eta_\theta = \frac{^{(a)}\rho_\theta}{^{(c)}\rho_\theta};$$

(d) converting said ratio of said active and control source power to noise variance ratios into a false-color or gray-scale functional image of source activity;

(e) coregistering said functional image with a predefined anatomical image; and, (f) displaying said coregistered images.

29. A method as defined in claim 14, further comprising the steps of:

(a) performing said steps 14(a) through 14(h) to determine an active source power and an active noise variance ratio while said subject's brain performs an activity task;

(b) performing said steps 14(a) through 14(h) to determine a control source power and a control noise variance ratio while said subject's brain performs a control task;

(c) for each of said voxels, deriving a function of the ratio of said active and control source power difference to the active and control noise variance sum:
$$^{(a-c)}T_\theta = \left[\frac{n|^{(a)}S_\theta^2 - {}^{(c)}S_\theta^2|}{^{(a)}\sigma_\theta^2 + {}^{(c)}\sigma_\theta^2}\right]^{1/2};$$

(d) converting said function of said active and control source power and noise variances into a false-color or gray-scale functional image of source activity;

(e) coregistering said functional image with a predefined anatomical image; and, (f) displaying said coregistered images.

* * * * *